US 9,894,944 B2

(12) United States Patent
Brooks et al.

(10) Patent No.: US 9,894,944 B2
(45) Date of Patent: Feb. 20, 2018

(54) PERSONAL THERMAL MANAGEMENT SYSTEM

(71) Applicant: VORBECK MATERIALS, Jessup, MD (US)

(72) Inventors: Louise Brooks, Washington, DC (US);
John Lettow, Washington, DC (US);
Dan Scheffer, Frederick, MD (US)

( * ) Notice: Subject to any disclaimer, the term of this patent is extended or adjusted under 35 U.S.C. 154(b) by 282 days.

(21) Appl. No.: 14/752,989

(22) Filed: Jun. 28, 2015

(65) Prior Publication Data

US 2016/0374411 A1 Dec. 29, 2016

Related U.S. Application Data

(60) Provisional application No. 62/018,592, filed on Jun. 28, 2014.

(51) Int. Cl.
| *A41D 13/005* | (2006.01) |
| *A61F 7/00* | (2006.01) |
| *A61F 7/02* | (2006.01) |

(52) U.S. Cl.
CPC ....... *A41D 13/0053* (2013.01); *A41D 13/005* (2013.01); *A41D 13/0051* (2013.01); *A61F 7/00* (2013.01); *A61F 7/007* (2013.01); *A61F 7/02* (2013.01); *A61F 2007/0056* (2013.01); *A61F 2007/0233* (2013.01)

(58) Field of Classification Search
CPC .............. A41D 13/0053; A41D 13/005; A41D 13/0051
See application file for complete search history.

(56) References Cited

U.S. PATENT DOCUMENTS

| 5,032,705 | A | 7/1991 | Batcheller | |
| 6,789,274 | B1* | 9/2004 | Karpati | A41D 13/0053 |
| | | | | 2/458 |
| 8,435,277 | B2 | 5/2013 | Schock | |
| 8,683,966 | B2 | 4/2014 | Allen | |
| 9,635,889 | B1* | 5/2017 | Copeland | A41D 13/0056 |
| 2005/0278819 | A1* | 12/2005 | Munn | A41D 13/0007 |
| | | | | 2/69 |
| 2010/0025009 | A1 | 2/2010 | Klett | |
| 2010/0107657 | A1 | 5/2010 | Vistakula | |
| 2010/0107991 | A1* | 5/2010 | Elrod | G01N 33/0004 |
| | | | | 119/712 |
| 2012/0124713 | A1* | 5/2012 | Blauer | F41H 1/02 |
| | | | | 2/102 |
| 2013/0204332 | A1* | 8/2013 | Amalfi | A61F 7/106 |
| | | | | 607/112 |
| 2016/0346571 | A1* | 12/2016 | Huber | A62B 35/0012 |

* cited by examiner

*Primary Examiner* — Ljiljana Ciric
(74) *Attorney, Agent, or Firm* — Trentice V. Bolar, Esq.

(57) ABSTRACT

Embodiments of the present invention relate to a wearable personal thermal management system and an associated method of manufacture. The PTMS comprises a harness that includes one or more cooling components and/or heating components. The harness include an upper-torso wearable portion and/or a lower-torso wearable portion. The PTSM provides a heating and/or cooling effects to one or more thermally sensitive areas of its user when worn.

20 Claims, 6 Drawing Sheets though the term has a physiological basis and can be considered to be identical with the term optimum temperature. Thermal comfort and discomfort typically reflects both internal (core) and external (skin) temperature sensitivity and the central integration of these two loops. When dealing with textile and allied assemblies, as in clothing, the factors contributing mainly to the external loop of the thermal comfort sensation are typically at play.

PERSONAL THERMAL MANAGEMENT SYSTEM

CROSS-REFERENCE TO RELATED APPLICATIONS

This application claims priority to U.S. Provisional Application No. 62/018,592 filed Jun. 28, 2014, which is incorporated herein by reference.

BACKGROUND

The present invention relates generally to thermal management and specifically to personal thermal management systems. Thermal comfort is a term created by psychologists; nevertheless the term has a physiological basis and can be considered to be identical with the term optimum temperature. Thermal comfort and discomfort typically reflects both internal (core) and external (skin) temperature sensitivity and the central integration of these two loops. When dealing with textile and allied assemblies, as in clothing, the factors contributing mainly to the external loop of the thermal comfort sensation are typically at play.

Skin is an organ that has a special role, as it is typically not only the source of information by virtue of comfort sensors, but the interface between the thermal core of the body and the environment. The human body attempts to maintain core body temperature around 37° C. The balance between perspiration and heat productions by the body and loss of the same may be defined as the "comfort" factor. The body is typically in a state of comfort when its temperature is about 35° C. and there is little to no moisture present on the skin. Heat exchange with the environment plays a key role in the thermal state of the human body. Thermal comfort may be defined as that condition of mind which expresses satisfaction with the thermal environment. Due to individual differences, specifying a thermal environment that will satisfy the thermal comfort of all can be a challenge.

DETAILED DESCRIPTION

Figure 1:
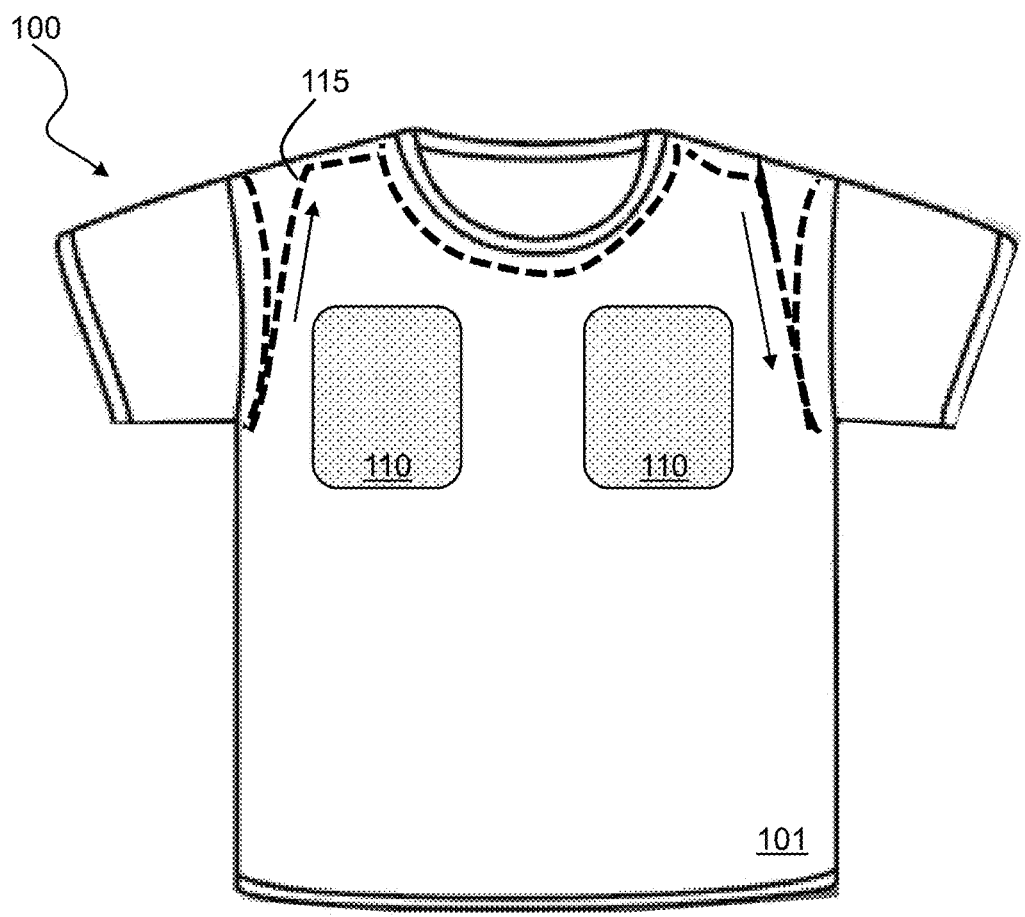
FIG. 1 depicts a frontal view of a personal thermal management system, generally 100, in accordance with an embodiment of the present invention.

The sensation of thermal comfort and discomfort can reflect a desired optimum and sub-optimum temperature, respectively, and often relies upon the individuals internal (core) and external (skin) temperature sensitivity and the central integration of these two loops. When dealing with textile and allied assemblies, as in clothing or bedding, the factors contributing mainly to the external loop of the thermal comfort sensation are typically at play.

Skin is the organ that typically plays a special role in thermal comfort and discomfort, as it is often a primary source of thermal information, as well as the interface between the thermal core of the body and the environment. The human body typically attempts to maintain core body temperature around 37° C. The balance between perspiration and heat productions by the body and loss of the same is often termed the "comfort" factor. The body is typically in a state of comfort when its temperature is about 35° C. and there is no moisture on the skin. Heat exchange with the environment plays a key role in the thermal state of the human body. Thermal comfort may be defined as condition of mind that expresses satisfaction with the thermal environment. Due to individual differences, specifying a thermal environment that addresses the thermal comfort of all persons present in a given area can be a challenge.

Personal thermal management systems of the present invention can improve a person's perceived thermal comfort. Embodiments of the present invention seek to provide a personal thermal management system (hereinafter "PTMS") that improves the wearer thermal comfort.

The PTMS of the present invention includes one or more cooling components and one or more heating components. Cooling elements can be positioned by the PTMS to be in thermal communication with regions of the skin of the wearer. Cooling component can selectively provide a cooling effect to the user of the PTMS (hereinafter "the wearer"). Heating component may be in thermal communication regions of the skin of wearer and selectively provide a heating effect thereto, PTMS's can be formed in a manner to target one or more thermally sensitive areas of the body, for example, the carotid artery, the axillae, the groin area, the arms, the back, the legs, the foot area, and the head area.

In other embodiments, the PTMS includes additional components (discussed further below), which include, but are not limited to, one or more computing devices that are in communication with the cooling components and/or the heating components, which allow the wearer to control the cooling components and/or heating components and thereby increase and/or maintain the wearer's thermal comfort regardless of the ambient temperature. In an embodiment, the wearer controls the computing devices wirelessly with another computing device.

The PTMSs can comprise garments, including but not limited to long- or short-sleeve shirts, jackets/coats, vests, tank tops, jump suits, unitards, bodices, trousers, shorts, hooded garments, socks, head apparel, gloves, mittens, wearable blankets, sleeved blankets, braces, undergarments, harnesses, body-worn padding, footwear, scarves, sashes, sweat shirts, belts, bullet-proof apparel, scuba diving suits, dresses, skirts, robes, apparel items, and insoles. The term "garment" may further include manufactured garments or the fibers that are used to manufacture the garments.

The cooling and/or heating elements may include one or more types of applicable phase change materials (hereinafter "PCM") or latent heat storage material. In general, PCMs have the ability to absorb heat as their physical state changes from a solid to a liquid or a liquid to a solid (depending on the materials utilized) within a particular temperature range. Certain PCM's change from solid to solid. PCM's can use latent heat of phase change for heating or cooling depending on the whether the phase change is exothermic or endo thermic.

In most materials, the phase changes are reversible so that the latent heat storage can be used for either heating or cooling depending on the temperature conditions. Thermal characteristics of PTMS's can be tailored by the choice of the PCM used. In response to a temperature decrease within the temperature range, PCMs release the stored heat into its proximate environment as it undergoes phase change. PCMs can include one or more hydrated inorganic salts, linear long chain hydrocarbons, polyethylene glycol, fatty acids, stearates, metals, carbon nanofibers, paraffin, waxes, plastic crystals, eutectics, eicosane, nonadecane, octadecane, heptadecane, hexadecane, 2,2-dimethyl-1,3-propanediol, 2-hydroxymethyl-2-methyl-1,3-propanediol, polyethylene glycol and combinations thereof.

The use of PCMs can allow PTMS's to exhibit automatic thermal acclimatizing properties that require no user input. Automatic thermal acclimatizing properties can provide wearers with improved thermal protection abilities against temperature fluctuations in the ambient environment.

For example, PCMs can exhibit an insulating effect that is dependent on temperature and time; takes place only during the phase change (within the temperature range of the phase change); and terminates when the phase change completes. Hence, in embodiments where one or more PCMs are included, the PTMS can react to changes in ambient temperatures across a broader temperature range compared to the use of one PCM. For example, in response to a rise in the ambient temperature and/or wearer's body temperature occurs, the PCM can react by undergoing a phase change and absorbing the heat. When the temperature falls again, the PCM undergoes a phase change back to the original state and, in the process, releases this stored heat.

PMCs may be incorporated into garments and articles using a plurality of applicable methods, which include, but are not limited to, coating, lamination, finishing, melt spinning, bicomponent synthetic fiber extrusion, infection molding, and foam techniques. The incorporation of PCMs may require microencapsulation, which is a process in which tiny particles or droplets of a material are surrounded by a coating to yield small capsules that can be used to incorporate the material on a micro metric scale. In an embodiment, PTMS's of the present invention include one or more PCMs that may or may not be microencapsulated.

PCMs may be formed as microcapsules that can be incorporated into or coated onto the synthetic and/or natural fibers that are used to form the final product (i.e. PTMS's, garments, and textiles) or may be applied to the fabrics subsequent to manufacture of the final product. Applicable synthetic and/or natural fibers include, but are not limited to, animal-based fibers, plant-based fibers, nylons and polyamides, rayon, poly(ethylene terephthalate) (PET), aramids, wool, silk, acetate, Tencel, acrylic, lyocell, spandex, modacryl polyolefins such as polyethylene, polypropylene, and poly(lactic acid)(PLA).

PCMs can be incorporated into the fibers using any suitable means. For example, they may be combined with monomers that are polymerized to form a polymer that is formed into fibers. They may be formed into a master batch with a polymer or other precursor that is to be formed into fibers and combined prior to or during a fiber formation process. They can be added directly to a polymer or other fiber precursor during the fiber formation process. They can be coated onto the fibers. For example, a coating for the garment can include wetted microspheres containing one or more PCMs dispersed throughout a polymer binder, and optionally one or more of a surfactant, a dispersant, an antifoam agent and a thickener.

Fibers may take on a variety of forms, including, staple fibers (also referred to as spun fibers), monofilaments, and multi-filaments. Fibers can be made using any suitable process, including extrusion, melt spinning, solvent (wet) spinning, dry spinning, gel spinning, reaction spinning, electrospinning. The fibers may be of any cross-sectional shape. For example, the fibers may have a circular or substantially circular cross-section, or have cross-sections that are, for example, oval, star-shaped, multi-lobed (including tri-lobed), square, rectangular, polygonal, irregular, etc. The fibers may also be hollow in their entirety or in part or be foamed. The fibers may be crimped, bent, twisted, woven or the like.

Fibers may be in the form of a multicomponent (such as a bicomponent) composite structure (these are also referred to as conjugate fibers), including multilayered structures comprising two or more concentric and/or eccentric layers (including inner core and outer sheath layers), a side-by-side structure, or the like. The multilayered structures can be obtained by, for example, extruding two or more polymers from the same spinnerette.

To prepare the coating, microspheres containing one or more PCMs can be wetted and dispersed in a dispersion of water solution containing a surfactant, a dispersant, an antifoam agent and a polymer mixture. The coating may then be applied to a textile substrate. Applicable coating processes include, but are not limited to, knife-over-roll, knife-over-air, pad-dry-cure, gravure, dip coating, and transfer coating. As per lamination, for example, microcapsules of one or more PCMs may be mixed into a water-blown polyurethane foam mix and these foams can subsequently be applied to a garment in a lamination process, wherein the water can be removed from the system by a drying process.

The required thermal insulation of garments may depend on the wearer's physical activity and/or on the surrounding conditions, such as temperature and relative humidity. The quantity of heat produced by wearers may substantially depend on their physical activity and can vary from 100 W while resting to over 1000 W during maximum physical performance. Heating and/or cooling components can be affixed to the outside, inside, and/or between layer of fabric. Heating and/or cooling components of the present invention may be positioned proximate to thermally sensitive areas (discussed above) to provide thermal comfort in an efficient manner that reduces or eliminates excessive heating and cooling to achieve the desired results. PTMS's that target thermally sensitive areas can be made lighter, thinner, and cheaper since less material and components are required to achieve desired results.

Figure 2:
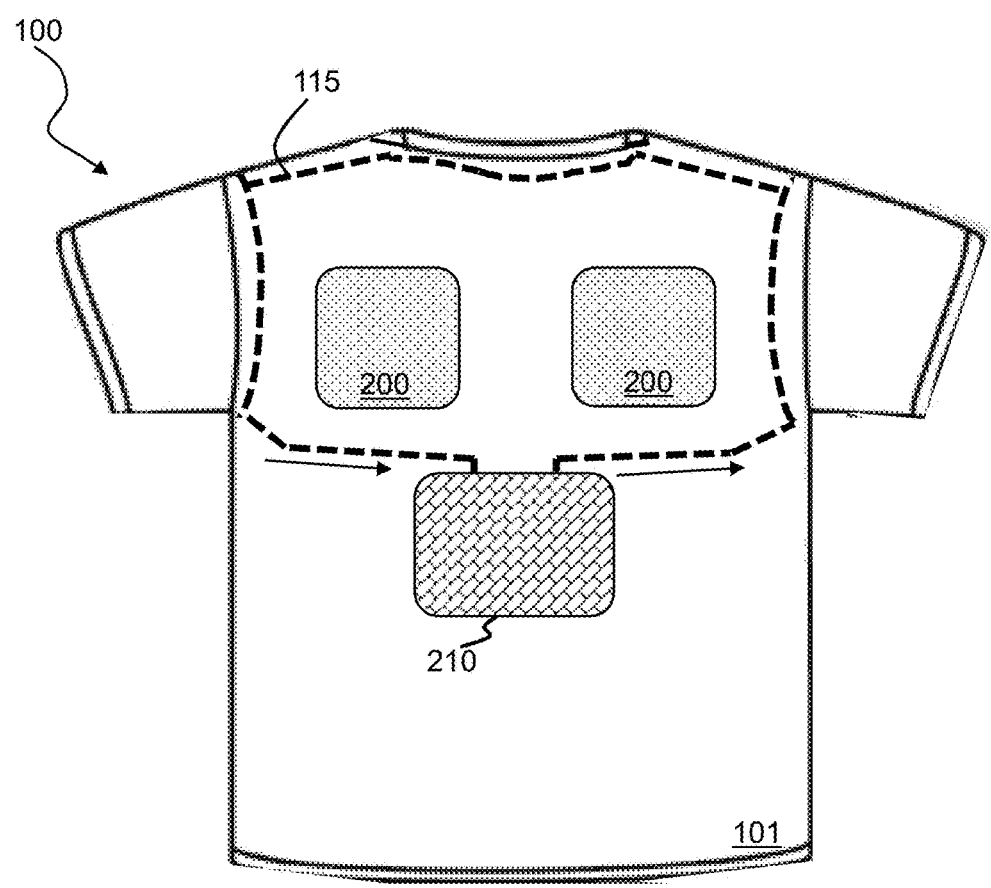
FIG. 2 depicts a back view of the personal thermal management system, in accordance with an embodiment of the present invention.

Non-limited embodiments of applicable PTMS, components, and methods of manufacture are discussed below. FIGS. 1 and 2 are discussed together in order to facilitate the description of PTMS 100. FIG. 1 depicts a frontal view of a PTMS, generally 100, in accordance with an embodiment of the present invention. PTMS 100 includes garment 101, tubing 115, and heaters 110 (discussed further below) both of which are strategically affixed to garment 101 proximate to corresponding thermally sensitive areas (i.e. the axillae, carotid artery, groin, and chest). Although not shown, garment 101 can be any of the aforementioned garments. FIG. 2 depicts a back view of PTMS 100, in accordance with an embodiment of the present invention. PTMS 100 can comprise cooling component 210, tubing 115, and heaters 200, in accordance with an embodiment of the present invention.

The heating and/or cooling components of the present invention can be used with alternating and direct current power sources, such as energy from an electrical grid, batteries (rechargeable and non-rechargeable), solar power, fuel cells, capacitors, solar power, and any combination thereof. The power source can be a low voltage power source such as one or more of a universal serial bus (hereinafter "USB™") port and battery, including but not limited to, a 12 V power supply and/or battery, a 24 and 42 V battery and power supply, a cell phone battery, a 9 V battery, a AAA battery, a AA battery, a laptop computer battery, a car battery, and a coin cell. Power may be supplied using a conventional wall plug or other source (e.g. a 12 V car battery), a USB™ power adapter, or a combination thereof, in accordance with an embodiment of the present invention.

Tubing 115 is a conveyance/conduit that is utilized by cooling component 210 to circulate a coolant/refrigerant around predetermined areas (such as thermally sensitive areas) of the wearer's body, in accordance with an embodiment of the present invention. Applicable coolants/refrigerants include, but are not limited to, nanofluids, thermofluids, water, R-134a, R-717, propane, butane, R-744, R-22, R-410A, hydrogen, helium, nitrogen, ammonia, and air. In an embodiment, applicable coolants/refrigerants have a coefficient of performance of 0.30. Tubing 115 circulates coolant/refrigerant around the axillae, shoulder region, and carotid artery, wherein the arrows depict the general direction of the flow.

Tubing 115 can circulate the coolant/refrigerant proximate to one or more of the carotid artery, axillae, groin area, arm area, back area, leg area, foot area, and head area. Cooling component 210 is an apparatus that provides, via tubing 115, a cooling sensation to the wearer, in accordance with an embodiment of the present invention. Cooling component 210, (hereinafter "the cooling element") can include one or more compressors, condensers, expansion valves, evaporators, tubing, coolants/refrigerants, and/or reservoirs. A coolant/refrigerant is utilized by the cooling component to provide a desired cooling effect. Although depicted as a dashed line, tubing 115 can include a plurality of tubes in various configurations, including, but not limited to, siamese and other multi-conjoined tubing. In an embodiment, tubing 115 is a muli-conjoined tubing that includes 2, 3, 4, 5, 6, or more tubes of one or more dimensions. In an embodiment, cooling element 210 includes a pulse pump to circulate a fluid, such as a coolant/refrigerant about the PTMS. PTMS 100 can comprise any number of copies of cooling component 210 to achieve a desired result.

PTMS 100 includes a pair of heater components 110 affixed proximate to the chest area (upper torso region) of garment 101. A pair of heater components 200 are also affixed to each side of the upper-back region of garment 101, as depicted in FIG. 2. Although not depicted, applicable heaters, such as heater 110, (hereinafter "heater") may be affixed to garment 101 utilizing any configuration and/or quantity to produce the desired effect. In an embodiment, one or more units of the heating components are affixed to the front, side, and/or back of the garment to provide thermal energy to one or more areas of the wearer's body (defined above). Although not depicted, heating and cooling components can be positioned adjacent to one another to target a particular area on the body and/or provide heating and cooling to the same areas.

Figure 3:
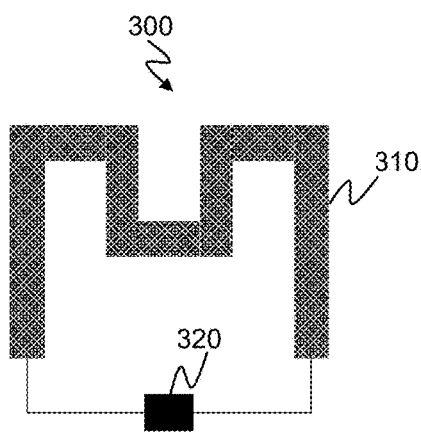
FIG. 3 illustrates a heater, generally 300, comprising graphene sheets, in accordance with an embodiment of the present invention.

FIGS. 3 through 7 depict various embodiments of applicable heaters. FIG. 3 illustrates heating component, generally 300, in accordance with an embodiment of the present invention. Heating component 300 comprises heating element 310, which is in electrical communication with voltage source 320. Heating element 310 can comprise a composition that includes graphene sheets and/or additional components (hereinafter "the composition"). Heating element 310 heats up in response to receiving voltage from voltage source 320. In an embodiment, heating element 310 is a busbar.

Figure 4:
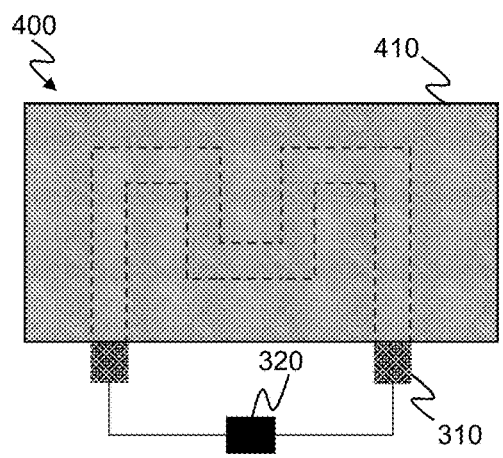
FIG. 4 illustrates an additional heater, generally 400, in accordance with an embodiment of the present invention.

In certain embodiments, the composition may be used to embed or cover all or part of the heating elements, such as heating element 310, thereby serving as a heat spreader. FIG. 4 illustrates an additional heating component, generally 400, in accordance with an embodiment of the present invention. Specifically, FIG. 4 depicts heating component 400, which comprises the same elements as heating component 300 in addition to coating 410, which can also include graphene sheets. Coating 410 can act as a heat spreader or diffuser.

The composition may further comprise one or more additional components, such as polymers and other thermally and/or electrically conductive materials (discussed further below). The composition can be a polymer composite, a coating, an ink, or the like. Applicable heating elements, such as heating element 310 and subsequently described heating elements, (hereinafter "the heating elements") can be formed from the composition using any suitable method, for example, they may be molded, extruded, printed, and/or applied in the form of a coating. The composition can be overmolded or coated onto the heating element. The heat elements can also be partially or fully embedded into the composition.

Figure 5:
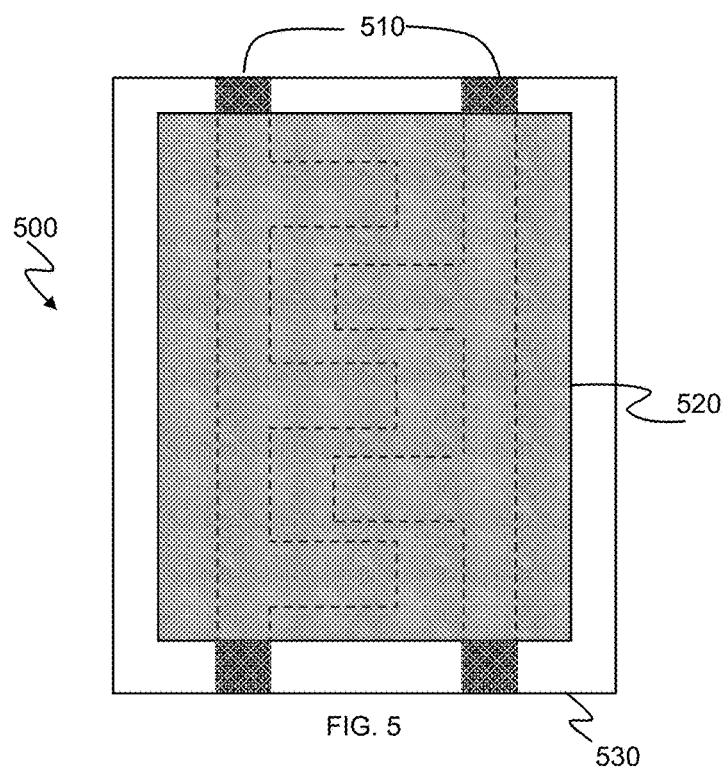
FIG. 5 illustrates an additional heater, generally 500, in accordance with an embodiment of the present invention.

FIG. 5 illustrates a heater, generally 500, in accordance with an embodiment of the present invention. Specifically, FIG. 5 depicts heating component 500, which comprises heating elements 510 and are printed on substrate 530 and overcoated with overcoat 520. Substrate 530 is discussed further below. Overcoat 520 includes the composition referenced above and discussed further below. In an embodiment, overcoat 520 heats up as a current is applied to heating elements 510. Overcoat 520 can serve as a heat spreader or diffuser.

Figure 6:
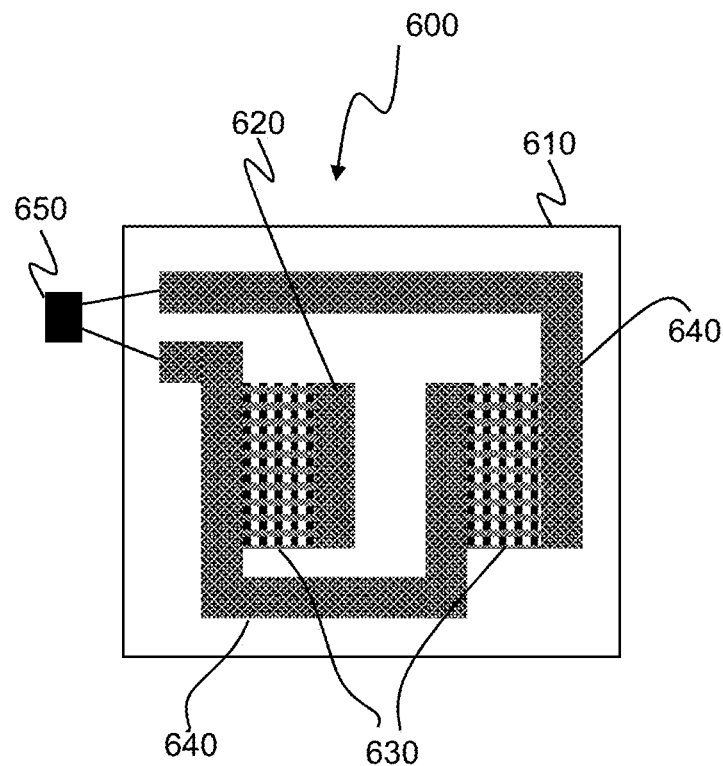
FIG. 6 illustrates an additional heater, generally 600, in accordance with an embodiment of the present invention.

FIG. 6 illustrates heating component, generally 600, in accordance with an embodiment of the present invention. Heating component 600, which comprises substrate 610 having coating 630 applied thereto. In an embodiment, coating 630 includes the composition. Coating 630 is overcoated with heating elements 640, which are in electrical communication with voltage source 650 and heating element 620. Heating elements 630 are not in communication with voltage source 650.

Figure 7:
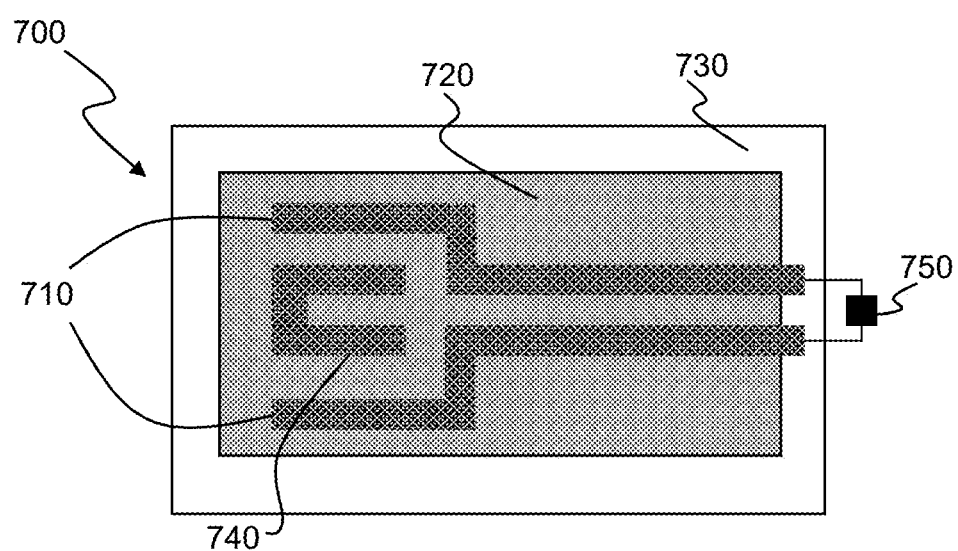
FIG. 7 illustrates an additional heater, generally 700, in accordance with an embodiment of the present invention.

FIG. 7 illustrates heating component, generally 700, in accordance with an embodiment of the present invention. Heating component 700, which comprises substrate 730 that is coated with coating 720. In an embodiment, coating 720 includes the composition. Coating 720 is overcoated with heating elements 710 and 740. Heating element component 740 is not in communication voltage source 750. Heating component 3, 4, 5, and 7 are structurally symmetrical. Heating component 6 is structurally non-symmetrical. The embodiments illustrated in FIGS. 1 to 7 are not limiting. Although not shown, applicable embodiments may include additional, less, and/or different components and/or connections than depicted herein. Heating elements 310, 510, 640, 620, 710, and 740 can perform similar functions and include similar materials and/or result from similar processes.

The heating components can also comprise one or more types of electrically conductive material, including, but not limited to, metals or metal alloys (e.g. copper, aluminum, silver, gold, and compositions thereof), organic, polymeric, and/or carbon-based conductors, coatings and/or inks. The electrically conductive material can be in any suitable form, including, but not limited to, strips, sheets, foils, tapes, wires, threads, and combinations thereof.

The heating elements can be formed by creating an electrical conductor, such as those disclosed herein, from a metallic (such as silver, copper, aluminum, steel, etc.) or non-metallic material and overcoating or overmolding the heating element with a form of the composition that is more electrically resistive than the heating element. Alternatively, the composition can be coated, molded over the more electrically conductive material. The composition can act as a heat spreader. Heating elements can also be formed from the composition. Heating elements include, but are not limited to a wire or filament, a trace, a printed trace, a metalized or plated surface, a metallic adhesive, an etch, or any combination thereof.

In general heating elements may be any heating element capable of providing thermal energy, in accordance with an embodiment of the present invention. Heating elements may have various geometric shapes and/or configurations, including, but not limited to, squared, rounded, circular, triangular, conical, spherical, convexical, polygonal, ellipsoidal, and/or any combination thereof. Heating elements can have any length, width, and/or depth suitable to achieve the desired effect, in accordance with an embodiment of the present innovation.

Heating elements may be affixed to the garment in a variety of configuration. For example, a series of heating elements can be utilized to provide a heating effect to the desired area of the wearer's body. Heating elements can be an element, device or component that is designed or used to generate, spread, disperse, handle, or manage the flow of heat, in accordance with an embodiment of the present invention. Heating elements can take the form of heaters, thermally conductive adhesives, thermally conductive gaskets and/or seals.

Heating elements may be in electrical communication with a voltage source, wherein heat is produced in response to the application of voltage to the heating elements. The operation of the heating elements may automatically initiate in response to an ambient temperature of less than 65° F.±8° F. (discussed further below). Heating elements may be comprised of a composition that includes graphene sheets (hereinafter "the composition").

Conductive materials can be deposited, such as by sputtering, plating, etching, molding, printing, coating, metallization, vapor deposition, adhering, gluing, taping, or other applicable deposition techniques, in accordance with an embodiment of the present invention. In some embodiments, the composition is applied to a substrate and overcoated with an ink or coating (e.g. silver, copper, or similar material) to form the heating elements. Alternatively, the heating elements can be formed on a substrate from an ink or coating and subsequently overcoated with the composition.

In other embodiments, predetermined regions of the substrate may be coated with the composition and overcoated with the element, while other predetermined regions of the substrate are coated with the element and overcoated with the composition. The resulting article can subsequently be laminated with additional materials and substrates and formed into the heating elements. The additional materials and substrates can be laminated on top of the coated surface (e.g. elements and the composition) or the heating element can be overcoated to create a sandwich structure. Applicable substrates can include fabrics, textiles, films, sheets, and other flexible substrates. In some cases, the laminated article can be thermally sealed.

The heating elements can be heat sinks, thermally conductive adhesives, thermal traces, heaters, coolers, passive solar heaters, such as hot water heaters, thermostats, thermally conductive channels, in accordance with an embodiment of the present invention.

The heating elements can be flexible, made to conform to a surface, crease resistant, and/or thin. The heating elements can be incorporated into or onto the garments utilizing any suitable method, such as by sewing, snaps, buttons, tape, adhesive, lamination, hook and loop fasteners (e.g. Velcro®), zippers, in accordance with an embodiment of the present invention. The heating elements can be embedded into the aforementioned garments permanently or they may be removable. The heating elements can be placed in, for example, pockets, slits, hems, between layers of components of the aforementioned system. The heating elements can be placed within the padding of the aforementioned garments. The heating elements can be sewn, taped, zipped, laminated, and/or any combination thereof, into place. In certain embodiments, the heating elements are washable.

The heating elements can be printed onto fabrics that comprise the aforementioned garments, wherein the fabrics can also be laminated with other fabric materials. The heating elements can have anisotropic thermal and/or electrical conductivities. The heating elements may be formed on a heat sealable substrate by any suitable method, including, but not limited to, printing, metal deposition, utilizing a conductive adhesive, applying cut, such as die-cut, shapes, or any combination thereof. In certain embodiments, the heating elements are overcoated at least in part with a coating containing the composition, wherein the coating composition is less thermally conductive than the heating element material. The heat sealable substrate containing the overcoated heating element can then adhered to one or more layers of other materials, such as fabrics. The resulting structure can be directly adhered to the aforementioned garments using various method, including, but not limited to, pressure and/or heat.

Examples of applicable electrically and/or thermally conductive additives include, but are not limited to, metals (including metal alloys), conductive metal oxides, conductive carbons, polymers, metal-coated materials, inorganic compounds, ceramics, and combinations thereof. The applicable electrically and/or thermally conductive additives can take a variety of forms, including, but not limited to, particles, powders, flakes, foils, needles, and combinations thereof.

Such metals can be pure metals and/or alloys. Examples of applicable metals include, but are not limited, to silver, copper, aluminum, platinum, palladium, nickel, chromium, gold, zinc, tin, iron, gold, lead, steel, stainless steel, rhodium, titanium, tungsten, magnesium, brass, bronze, and colloidal metals. Examples of applicable metal oxides include, but are not limited to, antimony tin oxide and indium tin oxide and materials such as fillers coated with metal oxides. Applicable metal and metal-oxide coated materials include, but are not limited to, metal coated carbon and graphite fibers, metal coated glass fibers, metal coated glass beads, metal coated ceramic materials (such as beads), and combinations thereof. The coating can be achieved with a variety of metals, including, but not limited to, nickel.

Figure 8:
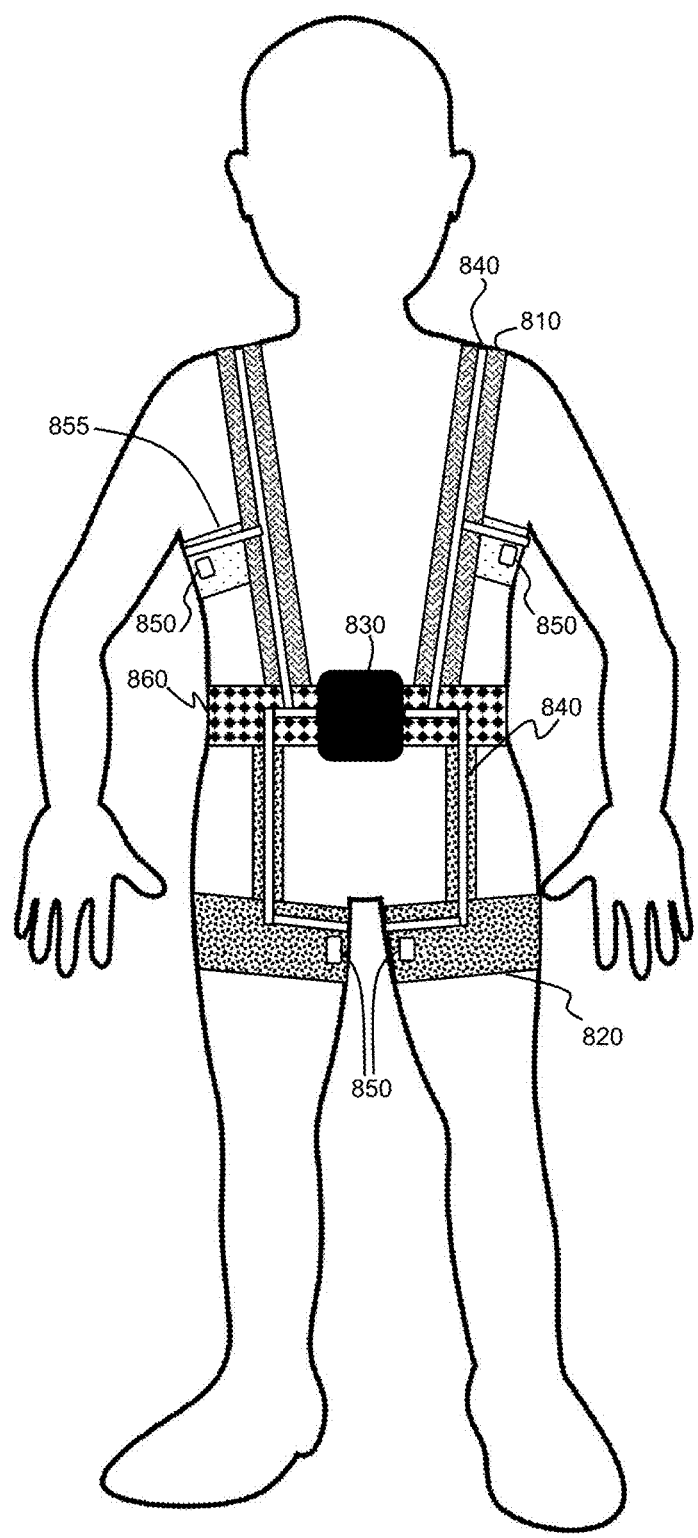
FIG. 8 depicts a personal thermal management system, in accordance with an embodiment of the present invention.

FIG. 8 depict a PTMS, generally 800, in accordance with an embodiment of the present invention. PTMS 800 is harness worn on the person of a human. PTMS 800 can be worn proximate to, adjacent to, or on to the wearer's skin. PTMS 800 can include an upper portion and/or a bottom portion. The upper portion is worn on the upper body of the wearer. The upper portion can comprise straps 855 that each connect to a strap 810. Straps 810 can also connect to strap 860. Straps 810 can be suspender-like structures that extend approximately from the front waist area to the shoulder area and down to the back waist area. Straps 810 can cross each other as they extend to the shoulder area. Straps 855 can connect two regions of strap 810. Straps 855 are positioned in a manner to locate heating and/or cooling components proximate to the axillae region. Strap 860 can a component that secures PTMS 800 to the waist area. The lower portion can comprise straps 820 connected to strap 860. Straps 820 secure PTMS 800 proximate to the groin area.

Straps 820 are components that secure heating and/or cooling elements proximate to the groin area of the wearer. PTMS can comprise electrical component 830. Electrical component 830 can a pump that circulates a thermal fluid, for example a refrigerant and coolants, about thermally sensitive areas of the wearer via conduit 840. Conduit 840 can be embedded within the straps in a manner that maintains its thermal functionality. Heating components 850 can be included in straps 820 and/or 855. Electrical component 830 can control heating components 850. Straps can comprise electrical wiring to enable electrical communication between electrical devices included in PTMS 800. The straps can comprise PCM's.

Straps can comprise insulating material that decrease the portion of cooling and/or heating lost to the ambient environment as opposed to being directed to the desired bodily regions. The upper and/or lower portions of PTMS 800 can be selectively or permanently incorporated within a garment.

Figure 9:
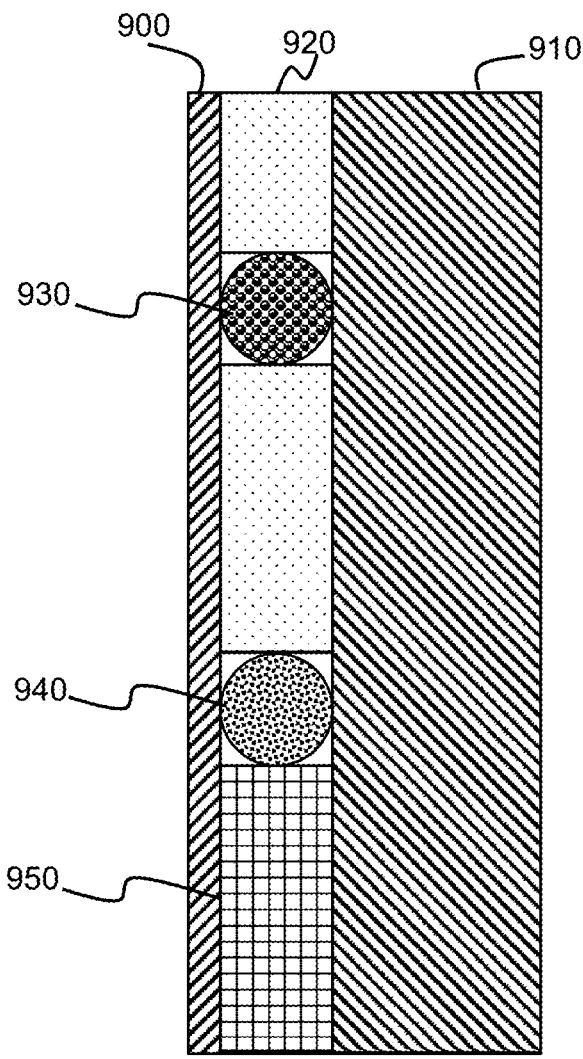
FIG. 9, illustrates a side through view of a portion of a personal thermal management system, in accordance with an embodiment of the present invention.

FIG. 9 illustrates a cross-section of a strap, in accordance with an embodiment of the present invention. The strap can comprise conduit 930, PCM 920, electrical line 940, and/or heating component 950 positioned between layers 900 and 910. Layer 900 can be a body-facing layer. Layer 900 can comprise a moisture wicking material. Layer 900 can comprise a non-abrasive material. Layer 900 can comprise a cushioning material. In general, layer 900 can comprise any material that does not reduce the effect of cooling and/or heating components. Conduit 930 can be utilized to convey a cooling fluid. Layer 910 can comprise an insulating material. Layers 900 and 910 can further comprise multiple types of materials and/or multiple layers.

Examples of applicable conductive polymers include, but are not limited to, polyacetylene, polyethylene dioxythiophene (PEDOT), poly(styrenesulfonate) (PSS), PEDOT:PSS copolymers, polythiophene and polythiophenes, poly(3-alkylthiophenes), poly(2,5-bis(3-tetradecylthiophen-2-yl)thieno[3,2-b]thiophene) (PBTTT), poly(phenylenevinylene), polypyrene, polycarbazole, polyazulene, polyazepine, polyflurorenes, polynaphthalene, polyisonaphthalene, polyaniline, polypyrrole, poly(phenylene sulfide), polycarbozoles, polyindoles, polyphenylenes, and copolymers of one or more of the foregoing, and their derivatives. The conductive polymers can be doped or undoped, for example, they can be doped with boron, phosphorous, iodine, and similar materials or combinations thereof.

Examples of applicable conductive carbons include, but are not limited to, graphite (including natural, Kish, and synthetic, annealed, pyrolytic, highly oriented pyrolytic, etc. graphites), graphitized carbon, carbon black, carbon fibers and fibrils, carbon whiskers, vapor-grown carbon nanofibers, metal coated carbon fibers, carbon nanotubes (including single- and multi-walled nanotubes), fullerenes, activated carbon, carbon fibers, expanded graphite, expandable graphite, graphite oxide, hollow carbon spheres, carbon foams, and combinations thereof.

Applicable thermally conductive additives (hereinafter "the thermally conductive additives") can be dielectrics. Such thermally conductive additives can be metal based. The thermally conductive additives can be electrically conducting, insulating or semiconducting. In some embodiments, the additives have electrical conductivities of no more than about $10^5$ S/cm, or of no more than about $10^4$ S/cm, or of no more than about $10^3$ S/cm, or of no more than about $10^2$ S/cm, or of no more than about 10 S/cm, or of no more than about 1 S/cm, or of no more than about 0.1 S/cm, or of no more than about $10^{-2}$ S/cm, or of no more than about $10^{-3}$ S/cm, or of no more than about $10^{-5}$ S/cm, or of no more than about $10^{-7}$ S/cm, or of no more than about $10^{-8}$ S/cm, or of no more than about $10^{-9}$ S/cm.

Examples of the thermally conductive additives include, but are not limited to, metal oxides, nitrides, ceramics, minerals, silicates, and/or combinations thereof. Additional examples of the thermally conductive additives include boron nitride, aluminum nitride, alumina, aluminum nitride, berylium oxide, nickel oxide, titanium dioxide, copper(I) oxide, copper (II) oxide, iron(II) oxide, iron(I,II) oxide (magnetite), iron (III) oxide, iron sulfide, iron(II) sulfide, silicon dioxide, zinc oxide, magnesium oxide (MgO), and/or any combination thereof.

In certain embodiments, the thermally conductive additives have a thermally conductivity at 25° C. of at least about 0.5 W/m·K, of at least about 0.7 W/m·K, of at least about 1 W/m·K, or at least about 3 W/m·K, or at least about 5 W/m·K, or at least about 10 W/m·K, or at least about 20 W/m·K, or at least about 30 W/m·K.

In certain embodiments, the composition comprises graphene sheets and at least one inorganic thermally conductive additive that is non-electrically conductive. Applicable non-electrically conductive additives can be metal based. In some embodiments, the aforementioned inorganic thermally conductive additive has a thermal conductivity at 25° C. of at least about 0.5 W/m·K, of at least about 0.7 W/m·K, of at least about 1 W/m·K, or at least about 3 W/m·K, or at least about 5 W/m·K, or at least about 10 W/m·K, or at least about 20 W/m·K, or at least about 30 W/m·K.

Applicable non-electrically conductive additives can be electrically insulating or semiconducting. In an embodiment, applicable non-electrically conductive additives have electrical conductivities of no more than about 105 S/cm, or of no more than about 104 S/cm, or of no more than about 103 S/cm, or of no more than about 102 S/cm, or of no more than about 10 S/cm, or of no more than about 1 S/cm, or of no more than about 0.1 S/cm, or of no more than about 10-2 S/cm, or of no more than about 10-3 S/cm, or of no more than about 10-5 S/cm, or of no more than about 10-7 S/cm, or of no more than about 10-8 S/cm, or of no more than about 10-9 S/cm.

Examples of applicable non-electrically conductive additives include, but are not limited to, metal oxides, nitrides, ceramics, minerals, silicates, etc. Such examples can further include boron nitride, aluminum nitride, alumina, aluminum nitride, berylium oxide, nickel oxide, titanium dioxide, copper(I) oxide, copper (II) oxide, iron(II) oxide, iron(I,II) oxide (magnetite), iron (III) oxide, iron sulfide, iron(II) sulfide, silicon dioxide, zinc oxide, magnesium oxide (MgO), and similar material.

Applicable graphene sheets (discussed above) are graphite sheets preferably having a surface area of from about 100 to about 2630 m2/g. In some embodiments, the applicable graphene sheets primarily, almost completely, or completely comprise fully exfoliated single sheets of graphite. Graphene sheets that are approximately ≤1 nm thick and are often referred to as "graphene". In other embodiments, at least a portion of the applicable graphene sheets can comprise partially exfoliated graphite sheets, in which two or more sheets of graphite have not been exfoliated from each other. Applicable graphene sheets can comprise mixtures of fully and partially exfoliated graphite sheets. The applicable graphene sheets are distinct from carbon nanotubes. Applicable graphene sheets can have a "platy" (e.g. two-dimensional) structure that is void of the needle-like structure of carbon nanotubes. In certain embodiments, the two longest dimensions of the applicable graphene sheets can each be at least about 10 times greater, or at least about 50 times greater, or at least about 100 times greater, or at least about 1000 times greater, or at least about 5000 times greater, or at least about 10,000 times greater than the shortest dimension (i.e. thickness) of the sheets.

The applicable graphene sheets are distinct from expanded, exfoliated, and vermicular, graphite, which has a layered or stacked structure wherein the layers are not separated from each other. In an embodiment, the aforementioned graphene sheets are not entirely comprised of carbon, but can include heteroatoms incorporated into the lattice or as part of functional groups attached to the lattice. The lattice need not be a perfect hexagonal lattice and may contain defects, including, but not limited to, five- and seven-membered rings.

The applicable graphene sheets can be formed using any suitable method, for example, they can be obtained from graphite (including, but not limited to, natural, Kish, and synthetic, annealed, pyrolytic, highly oriented pyrolytic, graphites), graphite oxide, expandable graphite, expanded graphite, and any combination thereof. The applicable graphene sheets may be obtained by the physical exfoliation of graphite, by, for example, peeling, grinding, milling, graphene sheets. The applicable graphene sheets made be made by sonication of precursors, such as graphite. The applicable graphene sheets may be made by opening carbon nanotubes.

The applicable graphene sheets may be made from inorganic precursors, such as silicon carbide. The applicable graphene sheets may be made by chemical vapor deposition, such as by reacting a methane and hydrogen on a metal surface. The applicable graphene sheets may be made by epitaxial growth on substrates such as silicon carbide and metal substrates and by growth from metal-carbon melts. The applicable graphene sheets can be made by the reduction of an alcohol, such ethanol, with a metal, such as an alkali metal like sodium, and the subsequent pyrolysis of the alkoxide product, such a method is reported in Nature Nanotechnology (2009), 4, 30-33 (herein incorporated by reference).

The applicable graphene sheets may be made from small molecule precursors such as carbon dioxide, alcohols, including, but not limited to ethanol, methanol, and similar materials, alkoxides, such as ethoxides, methoxides, sodium, potassium, and other alkoxides. Applicable graphene sheets may be made by the exfoliation of graphite in dispersions or by exfoliation of graphite oxide in dispersions and the subsequent reduction of the exfoliated graphite oxide. Applicable graphene sheets may be made by the exfoliation of expandable graphite, subsequently followed by intercalation, and ultrasonication or other means of separating the intercalated sheets as referenced in, for example, Nature Nanotechnology (2008), 3, 538-542 (herein incorporated by reference). The applicable graphene sheets may be made by the intercalation of graphite and the subsequent exfoliation of the resulting product in suspension, thermally and by similar processes. Applicable exfoliation processes may be thermal, and include exfoliation by rapid heating, using microwaves, furnaces, hot baths, and similar methods.

The applicable graphene sheets can be made from graphite oxide, which may also be referred to as "graphitic acid" or "graphene oxide". For example, graphite can be treated with oxidizing and/or intercalating agents and exfoliated. For example, graphite can be treated with intercalating agents and electrochemically oxidized and exfoliated. For example, graphene sheets can be formed by ultrasonically exfoliating suspensions of graphite and/or graphite oxide in a liquid, which can contain surfactants and/or intercalants. The resulting exfoliated graphite oxide dispersions or suspensions can be subsequently reduced to graphene sheets. Applicable graphene sheets can also be formed by mechanical treatment, including, but not limited to, grinding or milling, to exfoliate graphite or graphite oxide, which can subsequently be reduced to graphene sheets.

Applicable graphene sheets may be made by the reduction of graphite oxide. For example, the reduction of graphite oxide to graphene may be achieved by thermal reduction/annealing, chemical reduction, or similar process, and may be carried out on graphite oxide in a solid form, in a dispersion, or a combination thereof. Examples of useful chemical reducing agents include, but are not limited to, liquid or vapor hydrazines, such as N,N-dimethylhydrazine, and similar material, sodium borohydride, citric acid, hydroquinone, isocyanates, such as phenyl isocyanate, hydrogen, hydrogen plasma, or a combination thereof.

For example, a dispersion or suspension of exfoliated graphite oxide in a carrier, such as water, organic solvents, or a mixture of solvents, can be achieved using any suitable method, such as ultrasonication and/or mechanical grinding or milling, and reduced to graphene sheets. Such a reduction can be a solvothermal reduction, in solvents such as water, ethanol, or similar material. The aforementioned reduction can, for example, be achieved in an autoclave at elevated temperatures, such as those above about 200° C.

The aforementioned graphite oxide can be produced by any method known in the art, such as by an oxidation of graphite using one or more chemical oxidizing agents and, optionally, intercalating agents, such as sulfuric acid. Examples of applicable oxidizing agents include, but are not limited to, nitric acid, nitrates, such as sodium and potassium nitrates, perchlorates, potassium chlorate, sodium chlorate, chromic acid, potassium chromate, sodium chromate, potassium dichromate, sodium dichromate, hydrogen peroxide, sodium and potassium permanganates, phosphoric acid ($H_3PO_4$), phosphorus pentoxide, bisulfites, and combinations thereof.

In an embodiment, said oxidants include, but are not limited to, $KClO_4$; $HNO_3$ and $KClO_3$; $KMnO_4$ and/or $NaMnO_4$; $KMnO_4$ and $NaNO_3$; $K_2S_2O_8$ and $P_2O_5$ and $KMnO_4$; $KMnO_4$ and $HNO_3$; and $HNO_3$. In another embodiment, said intercalation agents include, but are not limited to, sulfuric acid. In an applicable method, graphite is treated with intercalating agents and electrochemically oxidized. Examples of methods of making graphite oxide include those described by Staudenmaier (Ber. Stsch. Chem. Ges. (1898), 31, 1481) and Hummers (J. Am. Chem. Soc. (1958), 80, 1339), herein incorporated by reference.

Applicable graphene sheets can be achieved by oxidizing graphite to graphite oxide, which is subsequently thermally exfoliated to form graphene sheets (also known as "thermally exfoliated graphite oxide"), as described in US 2007/0092432, the disclosure of which is hereby incorporated herein by reference. To be applicable, the thusly formed graphene sheets can display little or no signature corresponding to graphite or graphite oxide in their X-ray diffraction pattern. The aforementioned thermal exfoliation can be carried out in a continuous, semi-continuous batch, and/or similar process.

Heating for the thermal exfoliation can be done in a batch process or a continuous process and can be done under a variety of atmospheres, including inert and reducing atmospheres, which includes, but is not limited to, nitrogen, argon, and/or hydrogen atmospheres. Applicable heating times can range from under a few seconds or several hours or more, depending on the temperatures used and the characteristics desired in the final thermally exfoliated graphite oxide. The heating can be done in any appropriate vessel, such as a fused silica, mineral, metal, carbon (such as graphite), ceramic, or a combination thereof, vessel. The heating can be done using flash lamps or microwaves. For example, during heating, the graphite oxide can be contained in an essentially constant location in single batch reaction vessel, or transported through one or more vessels during the reaction in a continuous or batch mode. The heating can be done using any suitable means, including, but not limited to, the use of furnaces and infrared heaters.

Examples of temperatures at which the thermal exfoliation and/or reduction of graphite oxide can be carried out, include, but are not limited to at least about 150° C., at least about 200° C., at least about 300° C., at least about 400° C., at least about 450° C., at least about 500° C., at least about 600° C., at least about 700° C., at least about 750° C., at least about 800° C., at least about 850° C., at least about 900° C., at least about 950° C., at least about 1000° C., at least about 1100° C., at least about 1500° C., at least about 2000° C., and at least about 2500° C. In certain embodiments, the ranges include those that are between about 750 about and 3000° C., between about 850 and 2500° C., between about 950 and about 2500° C., between about 950 and about 1500° C., between about 750 about and 3100° C., between about 850 and 2500° C., or between about 950 and about 2500° C.

The time required for the heating can range from less than a second to one or more minutes. For example, the time can be less than about 0.5 seconds, less than about 1 second, less than about 5 seconds, less than about 10 seconds, less than about 20 seconds, less than about 30 seconds, or less than about 1 min. The time can be at least about 1 minute, at least about 2 minutes, at least about 5 minutes, at least about 15 minutes, at least about 30 minutes, at least about 45 minutes, at least about 60 minutes, at least about 90 minutes, at least about 120 minutes, at least about 150 minutes, at least about 240 minutes, from about 0.01 seconds to about 240 minutes, from about 0.5 seconds to about 240 minutes, from about 1 second to about 240 minutes, from about 1 minute to about 240 minutes, from about 0.01 seconds to about 60 minutes, from about 0.5 seconds to about 60 minutes, from about 1 second to about 60 minutes, from about 1 minute to about 60 minutes, from about 0.01 seconds to about 10 minutes, from about 0.5 seconds to about 10 minutes, from about 1 second to about 10 minutes, from about 1 minute to about 10 minutes, from about 0.01 seconds to about 1 minute, from about 0.5 seconds to about 1 minute, from about 1 second to about 1 minute, no more than about 600 minutes, no more than about 450 minutes, no more than about 300 minutes, no more than about 180 minutes, no more than about 120 minutes, no more than about 90 minutes, no more than about 60 minutes, no more than about 30 minutes, no more than about 15 minutes, no more than about 10 minutes, no more than about 5 minutes, no more than about 1 minute, no more than about 30 seconds, no more than about 10 seconds, or no more than about 1 second. During the course of the heating, the temperature can vary.

For example, the heating can be achieved at the rate of at least about 120° C./min, at least about 200° C./min, at least about 300° C./min, at least about 400° C./min, at least about 600° C./min, at least about 800° C./min, at least about 1000° C./min, at least about 1200° C./min, at least about 1500° C./min, at least about 1800° C./min, and/or at least about 2000° C./min.

Applicable graphene sheets can be annealed or reduced to graphene sheets having higher carbon to oxygen ratios by heating under reducing atmospheric conditions, for example, in systems purged with inert gases or hydrogen. Applicable reduction/annealing temperatures are preferably at least about 300° C., or at least about 350° C., or at least about 400° C., or at least about 500° C., or at least about 600° C., or at least about 750° C., or at least about 850° C., or at least about 950° C., or at least about 1000° C. The applicable reduction/annealing temperatures can be, for example, between about 750 about and 3000° C., or between about 850 and 2500° C., or between about 950 and about 2500° C.

Applicable heating times can be, for example, at least about 1 second, or at least about 10 second, or at least about 1 minute, or at least about 2 minutes, or at least about 5 minutes. In some embodiments, the applicable heating time is at least about 15 minutes, or about 30 minutes, or about 45 minutes, or about 60 minutes, or about 90 minutes, or about 120 minutes, or about 150 minutes. During the course of annealing/reduction, the temperature can vary within these ranges.

The heating can be achieved under a variety of conditions, including in an inert atmosphere, such as argon or nitrogen, or a reducing atmosphere, such as hydrogen, including, but not limited to, hydrogen diluted in an inert gas, such as argon or nitrogen, or it can be achieved under vacuum. The heating can be done in any appropriate vessel, such as a fused silica or a mineral or ceramic vessel or a metal vessel. For example, the materials heated (including any starting materials and any products or intermediates) can be contained in a substantially constant location in single batch reaction vessel, or can be transported through one or more vessels during the reaction in a continuous or batch reaction. The heating can be done using any suitable means, including the use of furnaces and infrared heaters.

Applicable graphene sheets preferably have a surface area of at least about 100 $m^2/g$ to, or of at least about 200 $m^2/g$, or of at least about 300 $m^2/g$, or of least about 350 $m^2/g$, or of least about 400 $m^2/g$, or of least about 500 $m^2/g$, or of least about 600 $m^2/g$, or of least about 700 $m^2/g$, or of least about 800 $m^2/g$, or of least about 900 $m^2/g$, or of least about 700 $m^2/g$. The surface area can be about 400 to about 1100 $m^2/g$. In an embodiment, the theoretical maximum applicable surface area is 2630 $m^2/g$. In another embodiment, the surface area includes all values and subvalues therebetween, especially including 400, 500, 600, 700, 800, 900, 1000, 1100, 1200, 1300, 1400, 1500, 1600, 1700, 1800, 1900, 2000, 2100, 2200, 2300, 2400, 2500, and 2630 $m^2/g$.

Applicable graphene sheets can have number average aspect ratios of about 100 to about 100,000, or of about 100 to about 50,000, or of about 100 to about 25,000, or of about 100 to about 10,000, wherein "aspect ratio" is defined as the ratio of the longest dimension of the sheet to the shortest.

Surface area can be measured using either the nitrogen adsorption/BET method at 77 K or a methylene blue (MB) dye method in liquid solution. The MB dye method can be carried out as follows: a known amount of graphene sheets is added to a flask; at least 1.5 g of MB are then added to the flask per gram of graphene sheets; ethanol is added to the flask and the mixture is ultrasonicated for about fifteen minutes; the ethanol is then evaporated and a known quantity of water is added to the flask to re-dissolve the free MB; and the undissolved material is allowed to settle, preferably by centrifuging the sample. The concentration of MB in solution can be determined using a UV-vis spectrophotometer by measuring the absorption at $\lambda_{max}$ of 298 nm relative to that of standard concentrations.

For example, the difference between the amount of MB that was initially added and the amount present in solution as determined by UV-vis spectrophotometry can be assumed to be the amount of MB that has been adsorbed onto the surface of the graphene sheets. The surface area of the graphene sheets may then calculated using a value of 2.54 $m^2$ of surface covered per 1 mg of MB adsorbed.

The applicable graphene sheets can have a bulk density of from about 0.01 to at least about 200 kg/m3. The bulk density thereof may include all values and subvalues therebetween, especially including 0.05, 0.1, 0.5, 1, 5, 10, 15, 20, 25, 30, 35, 50, 75, 100, 125, 150, and 175 $kg/m^3$.

Applicable graphene sheets can be used in a dry or powder form (with little or no solvent), as a blend/dispersion, and/or in one or more solvents.

Applicable graphene sheets can be functionalized with, for example, oxygen-containing functional groups, including, for example, hydroxyl, carboxyl, and epoxy groups. Such sheets typically have an overall carbon to oxygen molar ratio (hereinafter "C/O ratio"), as determined by bulk elemental analysis, of at least about 1:1, or more preferably, at least about 3:2. Examples of applicable C/O ratios include about 3:2 to about 85:15; about 3:2 to about 20:1; about 3:2 to about 30:1; about 3:2 to about 40:1; about 3:2 to about 60:1; about 3:2 to about 80:1; about 3:2 to about 100:1; about 3:2 to about 200:1; about 3:2 to about 500:1; about 3:2 to about 1000:1; about 3:2 to greater than 1000:1; about 10:1 to about 30:1; about 80:1 to about 100:1; about 20:1 to about 100:1; about 20:1 to about 500:1; about 20:1 to about 1000:1; about 50:1 to about 300:1; about 50:1 to about 500:1; and about 50:1 to about 1000:1. In an embodiments, the C/O ratio is at least about 10:1, or at least about 15:1, or at least about 20:1, or at least about 35:1, or at least about 50:1, or at least about 75:1, or at least about 100:1, or at least about 200:1, or at least about 300:1, or at least about 400:1, or at least 500:1, or at least about 750:1, or at least about 1000:1; or at least about 1500:1, or at least about 2000:1. Applicable C/O ratios also includes all values and subvalues between the aforementioned ranges.

Applicable graphene sheets can contain atomic scale kinks, which may be caused by the presence of lattice defects in, or by chemical functionalization of the two-dimensional hexagonal lattice structure of the graphite basal plane.

In certain embodiments, the composition further comprises graphite, which includes, but is not limited to, natural, Kish, and synthetic, annealed, pyrolytic, and highly oriented pyrolytic graphite. In some cases, the aforementioned graphite can be present in from about 1 to about 99 percent, or from about 10 to about 99 percent, or from about 20 to about 99 percent, from about 30 to about 99 percent, or from about 40 to about 99 percent, or from about 50 to about 99 percent, or from about 60 to about 99 percent, or from about 70 to about 99 percent, or from about 80 to about 99 percent, or from about 85 to about 99 percent, or from about 90 to about 99 percent, or from about 1 to about 95 percent, or from about 10 to about 95 percent, or from about 20 to about 95 percent, from about 30 to about 95 percent, or from about 40 to about 95 percent, or from about 50 to about 95 percent, or from about 60 to about 95 percent, or from about 70 to about 95 percent, or from about 80 to about 95 percent, or from about 85 to about 95 percent, or from about 90 to about 95 percent, or from about 1 to about 80 percent, or from about 10 to about 80 percent, or from about 20 to about 80 percent, from about 30 to about 80 percent, or from about 40 to about 80 percent, or from about 50 to about 80 percent, or from about 60 to about 80 percent, or from about 70 to about 80 percent, or from about 1 to about 70 percent, or from about 10 to about 70 percent, or from about 20 to about 70 percent, from about 30 to about 70 percent, or from about 40 to about 70 percent, or from about 50 to about 70 percent, or from about 60 to about 70 percent, or from about 1 to about 60 percent, or from about 10 to about 60 percent, or from about 20 to about 60 percent, from about 30 to about 60 percent, or from about 40 to about 60 percent, or from about 50 to about 60 percent, or from about 1 to about 50 percent, or from about 10 to about 50 percent, or from about 20 to about 50 percent, from about 30 to about 50 percent, or from about 40 to about 50 percent, or from about 1 to about 40 percent, or from about 10 to about 40 percent, or from about 20 to about 40 percent, from about 30 to about 40 percent, from about 1 to about 30 percent, or from about 10 to about 30 percent, or from about 20 to about 30 percent, or from about 1 to about 20 percent, or from about 10 to about 20 percent, or from about 1 to about 10 percent, based on the total weight of graphene sheets and graphite.

Applicable graphene sheets can comprise two or more graphene powders having different particle size distributions and/or morphologies. Applicable graphene sheets can comprise two or more graphite powders having different particle size distributions and/or morphologies.

For example, if one or more additional thermally and/or electrically conductive additives are used, they can be present in the composition in from about 1 to about 99 weight percent, or about 5 to about 95 weight percent, or about 5 to about 80 weight percent, or about 5 to about 70 weight percent, or about 5 to about 50 weight percent, or about 5 to about 35 weight percent, or about 15 to about 99 weight percent, or about 15 to about 95 weight percent, or about 15 to about 80 weight percent, or about 15 to about 70 weight percent, or about 15 to about 50 weight percent, or about 15 to about 35 weight percent, or about 30 to about 99 weight percent, or about 30 to about 95 weight percent, or about 30 to about 80 weight percent, or about 30 to about 70 weight percent, or about 30 to about 50 weight percent, or about 50 to about 99 weight percent, or about 50 to about 95 weight percent, or about 50 to about 80 weight percent, or about 50 to about 70 weight percent, or about 70 to about 99 weight percent, or about 70 to about 95 weight percent, or about 70 to about 80 weight percent, or about 80 to about 99 weight percent, or about 80 to about 95 weight percent, or about 90 to about 99 weight percent, or about 90 to about 95 weight percent, based on the total weight of the conductive additive and graphene sheets or graphene sheet and graphite, if present.

Applicable graphene sheets and other components can be combined with polymers to make composites, inks, coatings, laminates, foams, and similar materials. Applicable graphene sheets can be dispersed in one or more solvents with or without a polymer binder. The composition can be in the form of polymer composites, such as composites derived from thermoplastics and thermosetting polymers. The composition can be in the form of inks and coatings. As used herein, the terms "ink" and "coating" are reflective of compositions that are in a form that is suitable for application to a substrate as well as the material after it is applied to the substrate, while it is being applied to the substrate, and both before and after any post-application treatments, including, but not limited to, evaporation, cross-linking, curing, and similar processes. The components of the ink and coating compositions can vary during the aforementioned stages. The inks and coatings can optionally further comprise at least one polymeric binder. The inks and coatings can be in the form of paints.

Applicable polymeric binders can be thermosets, thermoplastics, non-melt processible polymers, and similar materials. Applicable polymeric binders can also comprise monomers that can be polymerized before, during, or after the application of the ink or coating to the substrate. Applicable polymeric binders can be crosslinked or otherwise cured after the coating has been applied to the substrate. Examples of applicable polymers include, but are not limited to, acrylic polymers, polyolefins (such as polyethylene, linear low density polyethylene (LLDPE), low density polyethylene (LDPE), high density polyethylene, polypropylene, and olefin copolymers), styrene/butadiene rubbers (SBR), styrene/ethylene/butadiene/styrene copolymers (SEBS), butyl rubbers, ethylene/propylene copolymers (EPR), ethylene/propylene/diene monomer copolymers (EPDM), polystyrene (including high impact polystyrene), poly(vinyl acetates), ethylene/vinyl acetate copolymers (EVA), poly(vinyl alcohols), ethylene/vinyl alcohol copolymers (EVOH), poly(vinyl butyral) (PVB), poly(vinyl formal), poly(methyl methacrylate) and other acrylate polymers and copolymers (such as methyl methacrylate polymers, methacrylate copolymers, polymers derived from one or more acrylates, methacrylates, ethyl acrylates, ethyl methacrylates, butyl acrylates, butyl methacrylates, glycidyl acrylates and methacrylates and the like), olefin and styrene copolymers, acrylonitrile/butadiene/styrene (ABS), styrene/acrylonitrile polymers (SAN), styrene/maleic anhydride copolymers, isobutylene/maleic anhydride copolymers, ethylene/acrylic acid copolymers, poly(acrylonitrile), poly(vinyl acetate) and poly(vinyl acetate) copolymers, poly(vinyl pyrrolidone) and poly(vinyl pyrrolidone) copolymers, vinyl acetate and vinyl pyrrolidone copolymers, polycarbonates (PC), polyamides, polyesters, liquid crystalline polymers (LCPs), poly(lactic acid) (PLA), poly(phenylene oxide) (PPO), PPO-polyamide alloys, polysulphones (PSU), polysulfides, polyetherketone (PEK), polyetheretherketone (PEEK), polyimides, polyoxymethylene (POM) homo- and copolymers, polyetherimides, fluorinated ethylene propylene polymers (FEP), poly(vinyl fluoride), poly(vinylidene fluoride), poly(vinylidene chloride), and poly(vinyl chloride), polyurethanes (thermoplastic and thermosetting (including crosslinked polyurethanes such as those crosslinked with amines, etc.), aramides (such as Kevlar® and Nomex®), polysulfides, polytetrafluoroethylene (PTFE), polysiloxanes (including polydimethylenesiloxane, dimethylsiloxane/vinylmethylsiloxane copolymers, vinyldimethylsiloxane terminated poly(dimethylsiloxane), etc.), elastomers, epoxy polymers (including crosslinked epoxy polymers such as those crosslinked with polysulfones, amines, etc.), decalin polymers, polyureas, alkyds, cellulosic polymers (such as nitrocellulose, ethyl cellulose, ethyl hydroxyethyl cellulose, carboxymethyl cellulose, cellulose acetate, cellulose acetate propionates, and cellulose acetate butyrates), polyethers (such as poly(ethylene oxide), poly(propylene oxide), poly(propylene glycol), oxide/propylene oxide copolymers, etc.), acrylic latex polymers, polyester acrylate oligomers and polymers, polyester diol diacrylate polymers, UV-curable resins, etc.

Examples of applicable elastomers include, but are not limited to, polyurethanes, copolyetheresters, rubbers (including butyl rubbers and natural rubbers), styrene/butadiene copolymers, styrene/ethylene/butadiene/styrene copolymer (SEBS), polyisoprene, ethylene/propylene copolymers (EPR), ethylene/propylene/diene monomer copolymers (EPDM), polysiloxanes, and polyethers (such as poly(ethylene oxide), poly(propylene oxide), and their copolymers).

Examples of applicable polyamides include, but are not limited to, aliphatic polyamides (such as polyamide 4,6; polyamide 6,6; polyamide 6; polyamide 11; polyamide 12; polyamide 6,9; polyamide 6,10; polyamide 6,12; polyamide 10,10; polyamide 10,12; and polyamide 12,12), alicyclic polyamides, and aromatic polyamides (such as poly(m-xylylene adipamide) (polyamide MXD,6)) and polyterephthalamides such as poly(dodecamethylene terephthalamide) (polyamide 12,T), poly(decamethylene terephthalamide) (polyamide 10,T), poly(nonamethylene terephthalamide) (polyamide 9,T), the polyamide of hexamethylene terephthalamide and hexamethylene adipamide, the polyamide of hexamethyleneterephthalamide, and 2-methylpentamethyleneterephthalamide), and similar materials. Applicable polyamides can be polymers and copolymers (i.e., polyamides having at least two different repeat units) having melting points between about 120 and 255° C., which includes, but is not limited to, aliphatic copolyamides having a melting point of about 230° C. or less, aliphatic copolyamides having a melting point of about 210° C. or less, aliphatic copolyamides having a melting point of about 200° C. or less, and aliphatic copolyamides having a melting point of about 180° C. or less. Examples of these polyamides include those sold under the trade names Macromelt™ by Henkel and Versamid™ by Cognis.

Examples of applicable acrylate polymers include those made by the polymerization of one or more acrylic acids (including acrylic acid, methacrylic acid, etc.) and their derivatives, such as esters. Examples applicable polyerms include methyl acrylate polymers, methyl methacrylate polymers, and methacrylate copolymers. Examples applicable polyerms include polymers derived from one or more acrylates, methacrylates, acrylic acid, methacrylic acid, methyl acrylate, methyl methacrylate, ethyl acrylate, ethyl methacrylate, butyl acrylate, butyl methacrylate, glycidyl acrylate, glycidyl methacrylates, 2-ethylhexyl acrylate, 2-ethylhexyl methacrylate, hydroxyethyl acrylate, hydroxyethyl (meth)acrylate, acrylonitrile, and similar material. The applicable polymers can comprise repeat units derived from other monomers such as olefins (e.g. ethylene, propylene, etc.), vinyl acetates, vinyl alcohols, vinyl pyrrolidones, etc. They can include partially neutralized acrylate polymers and copolymers (such as ionomer resins).

Examples of applicable polymers include, but are not limited to, Elvacite® polymers supplied by Lucite International, Inc., including Elvacite® 2009, 2010, 2013, 2014, 2016, 2028, 2042, 2045, 2046, 2550, 2552, 2614, 2669, 2697, 2776, 2823, 2895, 2927, 3001, 3003, 3004, 4018, 4021, 4026, 4028, 4044, 4059, 4400, 4075, 4060, 4102, and similar materials. Applicable polymer families include, but are not limited to, Bynel® polymers (such as Bynel® 2022 supplied by DuPont) and Joncryl® polymers (such as Joncryl® 678 and 682).

Applicable polyesters include, but are not limited to, poly(butylene terephthalate) (PBT), poly(ethylene terephthalate) (PET), poly(1,3-propylene terephthalate) (PPT), poly(ethylene naphthalate) (PEN), poly(cyclohexanedimethanol terephthalate) (PCT)), etc.

In some embodiments, applicable polymers have an acid number of at least about 5, or at least about 10, or at least about 15, or at least about 20.

In some embodiments, the glass transition temperature of at least one applicable polymer is no greater than about 100° C., 90° C., or no greater than about 80° C., or no greater than about 70° C., or no greater than about 60° C., or no greater than about 50° C., or no greater than about 40° C.

Examples of solvents into which the applicable graphene sheets and, optionally, other components can be dispersed include water, distilled or synthetic isoparaffinic hydrocarbons (such Isopar® and Norpar® (both manufactured by Exxon) and Dowanol® (manufactured by Dow), citrus terpenes and mixtures containing citrus terpenes (such as Purogen, Electron, and Positron (all manufactured by Ecolink)), terpenes and terpene alcohols (including terpineols, including alpha-terpineol), limonene, aliphatic petroleum distillates, alcohols (such as methanol, ethanol, n-propanol, i-propanol, n-butanol, i-butanol, sec-butanol, tert-butanol, pentanols, i-amyl alcohol, hexanols, heptanols, octanols, diacetone alcohol, butyl glycol, etc.), ketones (such as acetone, methyl ethyl ketone, cyclohexanone, i-butyl ketone, 2,6,8,trimethyl-4-nonanone etc.), esters (such as methyl acetate, ethyl acetate, n-propyl acetate, i-propyl acetate, n-butyl acetate, i-butyl acetate, tert-butyl acetate, carbitol acetate, etc.), glycol ethers, ester and alcohols (such as 2-(2-ethoxyethoxy)ethanol, propylene glycol monomethyl ether and other propylene glycol ethers; ethylene glycol monobutyl ether, 2-methoxyethyl ether (diglyme), propylene glycol methyl ether (PGME); and other ethylene glycol ethers; ethylene and propylene glycol ether acetates, diethylene glycol monoethyl ether acetate, 1-methoxy-2-propanol acetate (PGMEA); and hexylene glycol (such as Hexasol™ (supplied by SpecialChem)), dibasic esters (such as dimethyl succinate, dimethyl glutarate, dimethyl adipate), dimethylsulfoxide (DMSO), 1,3-dimethyl-3,4,5,6-tetrahydro-2(1H)-pyrimidinone (DMPU), imides, amides (such as dimethylformamide (DMF), dimethylacetamide, etc.), cyclic amides (such as N-methylpyrrolidone and 2-pyrrolidone), lactones (such as beta-propiolactone, gamma-valerolactone, delta-valerolactone, gamma-butyrolactone, epsilon-caprolactone), cyclic imides (such as imidazolidinones such as N,N'-dimethylimidazolidinone (1,3-dimethyl-2-imidazolidinone)) (DMI), aromatic solvents and aromatic solvent mixtures (such as toluene, xylenes, mesitylene, cumene, etc.), petroleum distillates, naphthas (such as VM&P naphtha), mixtures of two or more of the foregoing, and mixtures of one or more of the foregoing with other carriers. The solvents can be, for example, low- or non-VOC solvents, non-hazardous air pollution solvents, and non-halogenated solvents.

The composition can contain additives such as dispersion aids (including surfactants, emulsifiers, and wetting aids), adhesion promoters, thickening agents (including clays), defoamers and antifoamers, biocides, additional fillers, flow enhancers, stabilizers, crosslinking and curing agents, conductive additives, and similar materials.

Examples of applicable dispersing aids include glycol ethers (such as poly(ethylene oxide), block copolymers derived from ethylene oxide and propylene oxide (such as those sold under the trade name Pluronic® by BASF), acetylenic diols (such as 2,5,8,11-tetramethyl-6-dodecyn-5,8-diol ethoxylate and others sold by Air Products under the trade names Surfynol® and Dynol®), salts of carboxylic acids (including alkali metal and ammonium salts), and polysiloxanes.

Examples of applicable grinding aids include stearates (such as Al, Ca, Mg, and Zn stearates) and acetylenic diols (such as those sold by Air Products under the trade names Surfynol® and Dynol®).

Examples of applicable adhesion promoters include titanium chelates and other titanium compounds such as titanium phosphate complexes (including butyl titanium phosphate), titanate esters, diisopropoxy titanium bis(ethyl-3-oxobutanoate, isopropoxy titanium acetylacetonate, and others sold by Johnson-Matthey Catalysts under the trade name Vertec™.

The compositions can optionally comprise at least one "multi-chain lipid", by which term is meant a naturally-occurring or synthetic lipid having a polar head group and at least two nonpolar tail groups connected thereto. Examples of polar head groups include oxygen-, sulfur-, and halogen-containing, phosphates, amides, ammonium groups, amino acids (including α-amino acids), saccharides, polysaccharides, esters (Including glyceryl esters), zwitterionic groups, etc.

Applicable tail groups of the multi-chain lipids can be the same or different. Examples of applicable tail groups include alkanes, alkenes, alkynes, aromatic compounds, and similar formations. Applicable tail groups can be hydrocarbons, functionalized hydrocarbons, and similar materials. Applicable tail groups can be saturated or unsaturated. Applicable tail groups can be linear or branched. Applicable tail groups can be derived from fatty acids, such as oleic acid, palmitic acid, stearic acid, arachidic acid, erucic acid, arachadonic acid, linoleic acid, linolenic acid, oleic acid, and similar materials.

Examples of applicable multi-chain lipids include, but are not limited to, lecithin and other phospholipids (such as phosphatidylcholine, phosphoglycerides (including phosphatidylserine, phosphatidylinositol, phosphatidylethanolamine (cephalin), and phosphatidylglycerol) and sphingomyelin); glycolipids (such as glucosyl-cerebroside); saccharolipids; sphingolipids (such as ceramides, di- and triglycerides, phosphosphingolipids, and glycosphingolipids); and similar materials. Applicable multi-chain lipids can be amphoteric, including, but not limited to, zwitterionic.

Examples of applicable thickening agents include glycol ethers (such as poly(ethylene oxide), block copolymers derived from ethylene oxide and propylene oxide (such as those sold under the trade name Pluronic® by BASF), long-chain carboxylate salts (such aluminum, calcium, zinc, etc. salts of stearates, oleats, palmitates, etc.), aluminosilicates (such as those sold under the Minex® name by Unimin Specialty Minerals and Aerosil® 9200 by Evonik Degussa), fumed silica, natural and synthetic zeolites, and similar materials.

Examples of applicable crosslinking agents include radical initiators such as radical polymerization initiators, radical sources, etc., including organic and inorganic compounds. Coagents and crosslinking promoters may be used as well. Examples applicable coagents and crosslinking promoters include, but are not limited to, organic and inorganic peroxides (such as hydrogen peroxide, dialkyl peroxides, hydroperoxides, peracids, diacyl peroxides, peroxy esters, ketone peroxides, hydrocarbon peroxides, organometallic peroxides, organic polyoxides, organic polyoxides, dialkyl trioxides, hydrotrioxides, tetroxides, alkali metal peroxides (such as lithium peroxide), etc.), azo compounds, polyphenylhydrocarbons, substituted hydrazines, alkoxyamines, nitrocompounds, nitrates, nitrites, nitroxides, disulfides, polysulfides, persulfates (e.g. potassium persulfate, etc.), and similar materials.

Examples of applicable peroxides include, but are not limited to, dibenzoyl peroxide, dicumyl peroxide, acetone peroxide, methyl ethyl ketone peroxide, lauroyl peroxide, tert-butyl peroxide, tert-butyl peracetate, di-tert-amyl peroxide, tert-butyl hydroperoxide, cumene hydroperoxide, 1,3-bis-(tert-butylperoxy-1-propyl) benzene, bis-(tert-butylperoxy) valerate, bis-(2,4-dichlorobenzoyl) peroxide, and similar materials.

Examples of applicable azo compounds include, but are not limited to, azobisisobutylonitrile (AIBN); 1,1'-azobis (cyclohexanecarbonitrile) (ABCN); 2,2'-azobis(2-methylbutyronitrile); 2,2'-azobis(2-methylpropionitrile); 2,2'-azobis (2-methylpropionitrile); N-tert-butyl-N-(2-methyl-1-phenylpropyl)-O-(1-phenylethyl)hydroxylamine, and similar materials.

In certain embodiments, the composition includes aromatic compounds at least one aromatic ring. Applicable aromatic compounds may comprise two or more aromatic rings. When two or more aromatic rings are present, the rings may be fused, bonded directly to each other, and/or bonded using a spacer of one or more atoms. Applicable aromatic rings can be all-carbon based or can contain heteroatoms (heteroaromatics). Examples of rings systems the applicable aromatic compounds can be based on (derivatives of) include benzene, naphthalene, anthracene, tetracene, pentacene, phenanthrene, pyrene, pyrene, benzo[a] pyrene, coronene, chryrsene, triphenylene, perylene, corannulene, ovalene, acenaphthylene, fluorine, biphenyl, bisphenols, and similar compounds. Examples of heteroaromatic ring systems the applicable aromatic compounds can be based on include furan, thiophene, pyrrole, pyridine, indole, imidazole, pyrimidine, purine, and similar compounds. Applicable aromatic compounds can have a molecular weight of less than about 2000, less than about 1000, or less than about 500.

Applicable aromatic ring systems may be functionalized or multifunctional compounds that are substituted with one, two, or more functional groups, such as those that are nucleophilic or electrophilic. In some embodiments, the aromatic ring systems are capable of reacting with hydroxyl groups, carboxylic acids or carboxylic acid derivates, and/or epoxy groups. Examples of applicable functional groups include, but are not limited to, hydroxyls, hydroperoxy and peroxy groups, carboxylic acids, carboxylic acid salts (e.g. Li, Na, K, Mg, Ca, Zn, etc. salts), esters, anhydrides, acid halides (including acid chlorides), aldehydes (e.g. formyl groups), acetals, orthoesters, carbonates, amino groups, amides, imines, imides, azides, cyanates, isocyanates, thiol groups, sulfo, sulfino, thiocyanates, expoxies, ethers, and similar elements. In an embodiment, there are one, two, three, four, or more functional groups in the functionalized aromatic compound of the present invention.

Examples of applicable functional groups include, but are not limited to, compounds of the general formulas:

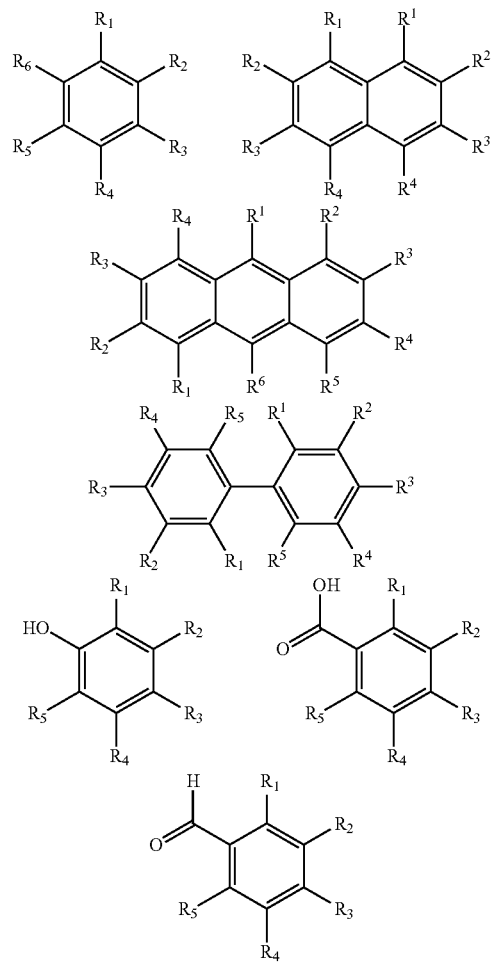

wherein the one or more of the substituents present (R1 to R5 and R1 to R6) can be a functional group or be substituted with a functional group. Additional substituents can be H, hydrocarbon groups (including alkyl, alkenyl, alkynyl, aryl, alicyclic, and similar groups), halides (e.g. chlorides, bromides, iodides, fluorides), and similar groups. The functional groups can be directly bonded to the aromatic ring. In some embodiments, when two or more aromatic rings are present, there can be at least one functional group present on two different rings.

Examples of applicable aromatic compounds include, but are not limited to, benzoic acid and benzoic acid derivatives, hydroxybenzoic acids (including 4-hydroxybenzoic acid), hydroxybenzaldehydes (including 4-hydroxybenzaldehyde), formylbenzoic acids (including 4-formylbenzoic acid), terephthaldehyde, isophthaldehyde, phthaldialdehyde, terephthalic acid (and esters such as methyl terephthalate, dimethyl terephthalate, etc.), isophthalic acid (and esters such as methyl isophthalate, dimethyl isophthalate, etc.), phthalic acid (and esters such as methyl phthalate, dimethyl phthalate, etc.), phthalic anhydride, bisphenols (such as bisphenol A), biphenyl, 4,4'-biphenyl, 3,3'-biphenyl, 2,2'-biphenyl, 4-hydroxybiphenyl, 3-hydroxybiphenyl, 2-hydroxybiphenyl, naphthalene, hydroxynaphthalenes, dihydroxynaphthalenes (including 2,6-dihydroxynaphthalene, 1,5-dihydroxynaphthalene, 2,3-dihydroxynaphthalene, 1,7-dihydroxynaphthalene, 1,4-dihydroxynaphthalene, 1,2-dihydroxynaphthalene, 1,3-dihydroxynaphthalene, 2,7-dihydroxynaphthalene, and 1,6-dihydroxynaphthalene), naphthalenecarboxylic acids, naphthalenecarboxylic acid esters, naphthalenedicarboxylic acids, naphthalenedicarboxylic acid esters, anthracene, pyrene, pentacene phenol, hydroquinone, catechol, resorcinol, and similar compounds.

In some embodiments, the applicable aromatic compounds can be present relative to the aforementioned graphene sheets in weight ratio of from about 0.1:99.9 to about 75:25, or of from about 0.5:99.5 to about 75:25, or of from about 0.5:99.5 to about 50:50, or of from about 0.5:99.5 to about 25:75, or of from about 0.5:99.5 to about 15:85, or of from about 0.5:99.5 to about 10:90, or of from about 0.5:99.5 to about 5:95, or of from about 1:99 to about 75:25, or of from about 1:99 to about 50:50, or of from about 1:99 to about 25:75, or of from about 1:99 to about 15:85, or of from about 1:99 to about 10:90, or of from about 1:99 to about 5:95, or of from about 2:98 to about 75:25, or of from about 2:98 to about 50:50, or of from about 2:98 to about 25:75, or of from about 2:98 to about 15:85, or of from about 2:98 to about 10:90, or of from about 2:98 to about 5:95, of from about 5:95 to about 50:50, of from about 5:95 to about 25:75, of from about 10:90 to about 75:25, of from about 10:90 to about 50:50, of from about 10:90 to about 25:75.

In other embodiments, the applicable aromatic compounds may react with the aforementioned graphene sheets and/or any polymeric binder that is present. Here, the applicable aromatic compound can serve to crosslink graphene sheets to itself and/or to the binder and/or crosslink the polymeric binder to itself. Such formulations can exhibit improved electrical conductivity and mechanical properties, which include, but are not limited to, improved adhesion when formed into inks or coatings and subsequently printed on a substrate.

The composition can be made using any suitable method, including, but limited to, wet or dry methods and batch, semi-continuous, and continuous methods. The composition can be made using melt-processing methods and solution/dispersion blending. Applicable melting-processing methods include, but are not limited to, a single or twin-screw extruder, a blender, a kneader, a Banbury mixer, and similar methods. Dispersions, suspensions, solutions, and similar formulations of the applicable graphene sheets and thermally conductive additives, including inks and coatings formulations, can be made or mechanically processed, for example, the formulation can be milled/ground, blended, dispersed, and/or suspended, using suitable mixing, dispersing, stirring, and/or compounding techniques, in accordance with an embodiment of the present invention.

Processing of the aforementioned components of the composition can be achieved in a variety of manners, including, but not limited to, milled/ground, and/or blended, by using suitable mixing, dispersing, and/or compounding techniques and apparatus, including ultrasonic devices, high-shear mixers, ball mills, attrition equipment, sandmills, two-roll mills, three-roll mills, cryogenic grinding crushers, extruders, kneaders, double planetary mixers, triple planetary mixers, high pressure homogenizers, horizontal and vertical wet grinding mills, and similar processing methods. Processing technologies, which include, but are not limited to, grinding, can be wet or dry as well as continuous or discontinuous.

Applicable materials for use as grinding media include, but are not limited to, metals, carbon steel, stainless steel, ceramics, stabilized ceramic media (such as cerium yttrium stabilized zirconium oxide), PTFE, glass, and tungsten carbide. Methods such as these can be used to change the particle size and/or morphology of the aforementioned components, such as, graphite, graphene sheets, thermally conductive additives, additional components, and blends thereof. The aforementioned components can be processed together or separately and can go through one or more processing (including mixing/blending) stages, wherein each stage involves one or more components as well as blends thereof.

There are no particular limitations in which the applicable graphene sheets, graphite, additives, and other components can be processed and combined. For example, the applicable graphene sheets and/or graphite can be processed into given particle size distributions and/or morphologies separately and then combined for further processing with or without the presence of additional components. Unprocessed graphene sheets and/or graphite can be combined with processed graphene sheets and/or graphite and further processed with or without the presence of additional components. Processed and/or unprocessed graphene sheets and/or processed and/or unprocessed graphite can be combined with additional components, such as one or more binders and then combined with processed and/or unprocessed graphene sheets and/or processed and/or unprocessed graphite. Two or more combinations of the processed and/or unprocessed graphene sheets and/or processed and/or unprocessed graphite that have been combined with other components can be further combined or processed.

Applicable graphene sheets and/or graphite can be processed (e.g. milled or ground) in the presence of the metal particles, or the graphene sheets and/or graphite can be processed separately from some or all of the thermally conductive additives, and the components later blended. The applicable graphene sheets and/or graphite and/or thermally conductive additives can be separately processed in the presence of binders and then later combined.

In some embodiment, where multi-chain lipids are used, it can be added to the applicable graphene sheets (and/or graphite if present) before processing. After the blending and/or grinding steps, additional components can be added to the compositions, including, but not limited to, thickeners, viscosity modifiers, and binders. The composition can also be diluted by the addition of more carrier Inks and coatings can be formed by blending the applicable graphene sheets with at least one solvent and/or binder, and, optionally, additional additives. The blending can be done using one or more of the preceding methods.

The composition can be formed by polymerizing monomers in the presence of the applicable graphene sheets and, optionally, additional additives. Polymer composite compositions can be made using any suitable melt-mixing method, such as those methods that utilize a single or twin-screw extruder, a blender, a kneader, or a Banbury mixer. In one embodiment, the composition is a melt-mixed blend, wherein the non-polymeric ingredients are well-dispersed in the polymer matrix, such that the blend forms a unified whole.

The aforementioned polymer composite compositions may be formed into thermal management devices using any suitable technique, including, but not limited to compression molding, extrusion, ram extrusion, injection molding, extrusion, co-extrusion, rotational molding, blow molding, injection blow molding, thermoforming, vacuum forming, casting, solution casting, centrifugal casting, overmolding, resin transfer molding, vacuum assisted resin transfer molding, spinning, and printing. Thermoset compositions of the applicable graphene sheets can be formed by mixing resin precursors with the applicable graphene sheets and, optionally, additional additives in a mold and curing.

Inks and coatings can be applied to a wide variety of substrates to form the heating element, including, but not limited to, flexible and/or stretchable materials, silicones and other elastomers and other polymeric materials, metals (which include, but are not limited to, aluminum, copper, steel, stainless steel), adhesives, heat-sealable materials (which include, but are not limited to, cellulose, biaxially oriented polypropylene (BOPP), poly(lactic acid), and polyurethanes), fabrics and textiles (which include, but are not limited to, cotton, wool, polyesters, and rayon), glasses and other minerals, ceramics, silicon surfaces, wood, paper, cardboard, paperboard, cellulose-based materials, glassine, labels, silicon and other semiconductors, laminates, corrugated materials, concrete, bricks, fiber-reinforced materials (which include, but are not limited to, glass fiber reinforced materials, glass fiber-reinforced epoxy resins, fiberglass, etc.), fiber mats, paper-reinforced phenolic resins, and building materials. Applicable substrates include, but are not limited to, films, papers, wafers, and three-dimensional objects.

Applicable substrates can be treated with additional coatings (such as paints) or similar materials prior to the application of the inks and coatings. For examples, applicable substrates, such as PET, may be coated with various materials, including, but not limited to, indium tin oxide, and antimony tin oxide. Applicable substrates can have a plurality of forms, including, but not limited to, woven, nonwoven, and mesh form. Applicable substrates can be woven, nonwoven, and/or in mesh form.

Applicable substrates can be paper-based materials that are, for example, surface treated, and/or impregnated. Examples of applicable surface treatments include, but are not limited to, coatings, such as polymeric coatings, which can include, but are not limited to, PET, polyethylene, polypropylene, biaxially oriented polypropylene (BOPP), acetates, and nitrocellulose. Applicable coatings can be adhesives. The paper based materials can be sized.

Examples of applicable polymeric materials include, but are not limited to, those comprising thermoplastics and thermosets, including elastomers and rubbers, phenolic resins, paper-reinforced phenolic resins, silicones, fluorinated polysiloxanes, natural rubber, butyl rubber, chlorosulfonated polyethylene, chlorinated polyethylene, styrene/butadiene copolymers (SBR), styrene/ethylene/butadiene/stryene copolymers (SEBS), styrene/ethylene/butadiene/stryene copolymers grafted with maleic anhydride, styrene/isoprene/styrene copolymers (SIS), polyisoprene, nitrile rubbers, hydrogenated nitrile rubbers, neoprene, ethylene/propylene copolymers (EPR), ethylene/propylene/diene copolymers (EPDM), ethylene/vinyl acetate copolymer (EVA), hexafluoropropylene/vinylidene fluoride/tetrafluoroethylene copolymers, tetrafluoroethylene/propylene copolymers, fluorelastomers, polyesters (including, but not limited to, poly(ethylene terephthalate), poly(butylene terephthalate), poly(ethylene naphthalate), liquid crystalline polyesters, and poly(lactic acid)), polystyrene, polyamides (including polyterephthalamides), polyimides (such as Kapton®), aramids (such as Kevlar® and Nomex®), fluoropolymers (such as fluorinated ethylene propylene (FEP), polytetrafluoroethylene (PTFE), poly(vinyl fluoride), poly (vinylidene fluoride), etc.), polyetherimides, poly(vinyl chloride), poly(vinylidene chloride), polyurethanes (such as thermoplastic polyurethanes (TPU)), spandex, cellulosic polymers (including, but not limited to, cellulose, nitrocellulose, cellulose acetate), styrene/acrylonitriles polymers (SAN), arcrylonitrile/butadiene/styrene polymers (ABS), polycarbonates, polyacrylates; poly(methyl methacrylate), ethylene/vinyl acetate copolymers, thermoset epoxies and polyurethanes; polyolefins (such as polyethylene (including low density polyethylene, high density polyethylene, and ultrahigh molecular weight polyethylene), polypropylene (including, but not limited to, biaxially-oriented polypropylene), and Mylar. Applicable substrates can be nonwoven materials, such as DuPont Tyvek®. Applicable substrates can be adhesive or adhesive-backed materials, including, but not limited to, adhesive-backed papers or paper substitutes. Applicable substrates can be mineral-based paper substitutes such as Teslin® from PPG Industries. Applicable substrates can comprise a transparent or translucent or optical material, such as glass, quartz, polymer (such as polycarbonate or poly(meth)acrylates (such as poly(methyl methacrylate).

The inks and coatings can be applied to applicable substrates using any suitable method, including, but not limited to, painting, pouring, spin casting, solution casting, dip coating, powder coating, by syringe or pipette, spray coating, curtain coating, lamination, co-extrusion, electrospray deposition, ink jet printing, spin coating, thermal transfer (including laser transfer) methods, doctor blade printing, screen printing, rotary screen printing, gravure printing, lithographic printing, intaglio printing, digital printing, capillary printing, offset printing, electrohydrodynamic (EHD) printing (as described in WO 2007/053621, which is hereby incorporated herein by reference), microprinting, pad printing, tampon printing, stencil printing, wire rod coating, drawing, flexographic printing, stamping, xerography, microcontact printing, dip pen nanolithography, laser printing, via pen, via brush, via sponge, or similar means. The compositions can be applied in multiple layers.

Subsequent to application to an applicable substrate, the inks and coatings can be cured using any suitable technique, including, but not limited to, drying and oven-drying (for example, in air or another inert or reactive atmosphere), UV curing, IR curing, drying, crosslinking, thermal curing, laser curing, IR curing, microwave curing or drying, sintering, and the like.

The cured inks and coatings can have a variety of thicknesses, for example, they can optionally have a thickness of at least about 2 nm, or at least about 5 nm. In various embodiments, the inks and coatings can optionally have a thickness of about 2 nm to 2 mm, about 5 nm to 1 mm, about 2 nm to about 100 nm, about 2 nm to about 200 nm, about 2 nm to about 500 nm, about 2 nm to about 1 micrometer, about 5 nm to about 200 nm, about 5 nm to about 500 nm, about 5 nm to about 1 micrometer, about 5 nm to about 50 micrometers, about 5 nm to about 200 micrometers, about 10 nm to about 200 nm, about 50 nm to about 500 nm, about 50 nm to about 1 micrometer, about 100 nm to about 10 micrometers, about 1 micrometer to about 2 mm, about 1 micrometer to about 1 mm, about 1 micrometer to about 500 micrometers, about 1 micrometer to about 200 micrometers, about 1 micrometer to about 100 micrometers, about 50 micrometers to about 1 mm, about 100 micrometers to about 2 mm, about 100 micrometers to about 1 mm, about 100 micrometers to about 750 micrometers, about 100 micrometers to about 500 micrometers, about 500 micrometers to about 2 mm, or about 500 micrometers to about 1 mm.

When applied to an applicable substrate, the inks and coatings can have a variety of forms, including, but not limited to, a film or lines, patterns, letters, numbers, circuitry, logos, identification tags, and other shapes and forms. The inks and coatings can be covered in whole or in part with additional material, including, but not limited to, overcoatings, varnishes, polymers, and fabrics. The inks and coatings can be applied to applicable substrates in varying thicknesses at different points and can be used to build up three-dimensional structures on the substrate.

The compositions can be thermally conductive and possess a thermal conductivity of about 0.1 to about 50 W/m·K, or of about 0.5 to about 30 W/m·K, or of about 0.1 to about 0.5 W/m·K, or of about 0.1 to about 1 W/m·K, or of about 0.1 to about 5 W/m·K, or of about 0.5 to about 2 W/m·K, or of about 1 to about 5 W/m·K, or of about 0.1 to about 0.5 W/m·K, or of about 0.1 to about 50 W/m·K, or of about 1 to about 30 W/m·K, or of about 1 to about 20 W/m·K, or of about 1 to about 10 W/m·K, or of about 1 to about 5 W/m·K, or of about 2 to about 25 W/m·K, or of about 5 to about 25 W/m·K, or of at least about 0.7 W/m·K, or of at least 1 W/m·K, or of at least 1.5 W/m·K, or of at least 3 W/m·K, or of at least 5 W/m·K, or of at least 7 W/m·K, or of at least 10 W/m·K, or of at least 15 W/m·K.

Disclosed herein is a wearable PTMS and an associated method of manufacture. The PTMS comprises a harness that can include cooling components and/or heating components. The harness can include an upper-torso wearable portion and/or a lower-torso wearable portion. The PTSM can provide heating and/or cooling effects to thermally sensitive areas of its user when worn. The harness can include phase change material that absorbs thermal energy when the ambient temperature exceeds a predetermined threshold and/or releases thermal energy when the ambient temperature falls below a second predetermined temperature threshold. The thermally sensitive area is proximate to one or more of the following areas: a carotid artery area, an axilla area, a groin area, an arm area, a back area, a chest area, an abdominal area, a leg area, a foot area, and a head area.

The cooling component can comprise a pulse pump. The PTMS can further comprise computing devices that control cooling components and/or heating components. The heating components can comprise graphene sheets. The upper-torso wearable portion and/or the lower-torso wearable portion can comprises straps formed in a manner to wrap around at least a portion thereof. The harness can comprise fluid conduits that are used by the cooling components to transport a coolant. The harness can include leg loops and/or shoulder straps. The harness can be formed in a manner to be selectively removable from a garment (i.e. the garment includes a removable PTMS).

The phase change material can include one or more of a hydrated inorganic salt, a linear long chain hydrocarbon, polyethylene glycol, a fatty acid, a stearate, a metal, a carbon nanofibers, paraffin, a wax, a plastic crystal, a eutectic composition, an eicosane, nonadecane, octadecane, heptadecane, hexadecane, 2,2-dimethyl-1,3-propanediol, 2-hydroxymethyl-2-methyl-1,3-propanediol, and polyethylene glycol. Cooling components can utilize one or more of a nanofluid, a thermofluid, water, R-134a, R-717, propane, butane, R-744, R-22, R-410A, hydrogen, helium, nitrogen, ammonia, and air to provide the cooling effect. The harness can comprise one or more computing devices that control the cooling components and/or the heating components. The cooling components and/or the heating components can be wirelessly controlled by one or more computing devices. The harness can be formed in a manner to be permanently included a garment.

What is claimed is:

1. A wearable personal thermal management system (PTMS) comprising:
    a harness comprising an upper portion and a bottom portion;
    wherein
        the upper portion comprises a first strap configured to be worn proximate to an axillae region of a wearer of the PTMS;
        the bottom portion comprises a second strap configured to be worn proximate to a groin area of the wearer; and
        at least one of the first strap and the second strap comprise a cooling component and a heating component.

2. The wearable personal thermal management system of claim 1, wherein the at least one of the first strap and the second strap comprise a phase change material configured to absorbs thermal energy when an ambient temperature exceeds a predetermined threshold and/or releases thermal energy when the ambient temperature falls below a second predetermined temperature threshold.

3. The wearable personal thermal management system of claim 1, wherein the thermally sensitive area is proximate to one or more of the following areas: a carotid artery area, an axilla area, a groin area, an arm area, a back area, a chest area, an abdominal area, a leg area, a foot area, and a head area.

4. The wearable personal thermal management system of claim 1, wherein the cooling component comprises a pulse pump configured to circulate a coolant.

5. The wearable personal thermal management system of claim 1, further comprising a computing device communicatively coupled to control the cooling component and/or the heating component.

6. The wearable personal thermal management system of claim 1, wherein the heating component comprises a composition comprising graphene sheets and a polymer.

7. The wearable personal thermal management system of claim 1, wherein the heating component comprises one or more of a thermally conductive adhesive, a thermally conductive gasket, and a thermally conductive seal.

8. The wearable personal thermal management system of claim 1, wherein at least one of the first strap and the second strap comprises a fluid conduit configured to circulate a coolant.

9. The wearable personal thermal management system of claim 1, wherein the cooling component utilizes a coolant comprising a coefficient of performance of 0.30 harness.

10. The wearable personal thermal management system of claim 1, wherein the harness is formed in a manner to be selectively removable from a garment.

11. The wearable personal thermal management system of claim 2, wherein the phase change material comprises at least one of a hydrated inorganic salt, a linear long chain hydrocarbon, polyethylene glycol, a fatty acid, a stearate, a metal, a carbon nanofibers, paraffin, a wax, a plastic crystal, a eutectic composition, an eicosane, nonadecane, octadecane, heptadecane, hexadecane, 2,2-dimethyl-1,3-propanediol, 2-hydroxymethyl-2-methyl-1,3-propanediol, and polyethylene glycol.

12. The wearable personal thermal management system of claim 1, wherein the harness comprises a computing device that controls the cooling component and/or the heating component.

13. The wearable personal thermal management system of claim 1, wherein the cooling component and/or the heating component are wirelessly controlled by a computing device.

14. The wearable personal thermal management system of claim 1, wherein the cooling component utilizes one or more of a nanofluid, a thermofluid, water, R-134a, R-717, propane, butane, R-744, R-22, R-410A, hydrogen, helium, nitrogen, ammonia, and air to provide a cooling effect.

15. The wearable personal thermal management system of claim 1, wherein the harness is formed in a manner to be permanently included a garment.

16. A method for forming a wearable personal thermal management system comprising:
    forming a harness comprising an upper portion and a bottom portion;
    wherein
        the upper portion comprising a first strap configured to be worn proximate to an axillae region of a wearer;
        the bottom portion comprising a second strap configured to be worn proximate to the wearer's groin area; and
        the first strap and the second strap each comprise a cooling component and a heating component.

17. The method of claim 16, wherein the at least one of the first strap and the second strap comprises a phase change material configured to absorb thermal energy when an ambient temperature exceeds a first predetermined temperature threshold and/or releases thermal energy when the ambient temperature falls below a second predetermined temperature threshold.

18. The method of claim 16, wherein the thermally sensitive area is proximate to one or more of the following areas: a carotid artery area, an axilla area, a groin area, an arm area, a back area, a chest area, an abdominal area, a leg area, a foot area, and a head area.

19. The method of claim 16, further comprising positioning a fluid conduit within at least one of the first strap and the second strap; and wherein fluid conduit is configured to circulate a coolant.

20. The method of claim 16, wherein the harness is formed in a manner to be selectively removable from a garment or permanently included in the garment.

* * * * *